United States Patent
Cao et al.

[11] Patent Number: 6,120,793
[45] Date of Patent: Sep. 19, 2000

[54] METHODS OF TREATING CANCER USING THESE DERIVATIVES

[75] Inventors: Zhisong Cao, Friendswood; Beppino C. Giovanella, Houston, both of Tex.

[73] Assignee: The Stehlin Foundation for Cancer Research, Houston, Tex.

[21] Appl. No.: 09/345,062

[22] Filed: Jun. 30, 1999

Related U.S. Application Data

[63] Continuation of application No. 09/030,357, Feb. 25, 1998, Pat. No. 5,968,943, and a continuation-in-part of application No. 08/594,235, Jan. 30, 1996, Pat. No. 5,731,316, and application No. PCT/US97/01728, Jan. 29, 1997.

[51] Int. Cl.$^7$ ............ A61F 13/00; A61K 47/00; A01N 43/42
[52] U.S. Cl. ............ 424/449; 424/443; 424/439; 514/283
[58] Field of Search .................. 424/448, 449, 424/443, 439; 514/283

[56] References Cited

U.S. PATENT DOCUMENTS

Re. 32,518  10/1987  Miyasaka et al. .
3,894,029  7/1975  Winterfeldt et al. .

(List continued on next page.)

FOREIGN PATENT DOCUMENTS

| 0 538 534 | 4/1993 | European Pat. Off. . |
| 30 26 172 | 2/1981 | Germany . |
| 56-108787 | 8/1981 | Japan . |
| 64-61482 | 3/1989 | Japan . |
| 92/05785 | 4/1992 | WIPO . |
| 94/19353 | 9/1994 | WIPO . |

OTHER PUBLICATIONS

Fessenden et al., "Techniques and Experiments for Organic Chemistry," PWS Publishers, 1983, ISBN 0–8175–0755–2, pp. 56–59.

Van Nostrand's Scientific Encyclopedia 7th Ed. (vol. 1)(1989), pp. 625–627.
McGraw Hill Encyclopedia of Science and Technology, vol. 3, 5th Ed., 1982, pp. 142–146.
Wani et al., *J. Med. Chem.*, vol. 23, pp. 554–560, 1980.
Wani et al., *J. Med. Chem.*, vol. 29, pp. 2358–2363, 1986.
Wall et al., *J. Med. chem.*, vol. 29, pp. 1553–1555, 1986.
Akimoto et al., *J. Chromatography*, vol. 588, pp. 165–170, 1991.
Gunasekera et al., *J. Natural Products (Lloydia)*, vol. 42, No. 5, pp. 475–477, 1979.
Sakato et al., *Agricultural and Biological chemistry*, vol. 38, No. 1, pp. 217–218, 1974.
Barilero et al., *J. Chromatography*, vol. 575, pp. 275–280 (1992).

(List continued on next page.)

*Primary Examiner*—Thurman K. Page
*Assistant Examiner*—Isis Ghali
*Attorney, Agent, or Firm*—Kilyk & Bowersox, P.L.L.C.

[57] ABSTRACT

Derivatives of camptothecin are disclosed and are represented by the general formula:

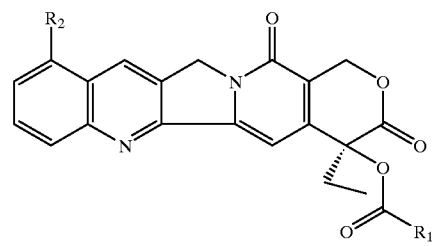

wherein when $R_2$ is H, $R_1$ is a $C_2$–$C_4$ alkyl group, a $C_6$–$C_{15}$ alkyl group, a $C_3$–$C_8$ cycloalkyl group, a $C_2$–$C_{15}$ alkenyl group or a $C_2$–$C_{15}$ epoxy group; and when $R_2$ is a nitro group, $R_1$ is a $C_1$–$C_{15}$ alkl group, a $C_2$–$C_{15}$ alkenyl group, a $C_3$–$C_8$ cycloalkyl group, or an epoxy group. Processes for making these derivatives and for using them in cancer treatment are also disclosed.

39 Claims, 21 Drawing Sheets

Mouse CPT Plasma Levels
2 MG/KG, I.S.

U.S. PATENT DOCUMENTS

| | | |
|---|---|---|
| 4,399,282 | 8/1983 | Miyasaka et al. . |
| 4,473,692 | 9/1984 | Miyasaka et al. . |
| 4,894,456 | 1/1990 | Wall et al. . |
| 4,914,205 | 4/1990 | Sawada et al. . |
| 4,943,579 | 7/1990 | Vishnuvajjala . |
| 5,053,512 | 10/1991 | Wani et al. . |
| 5,106,742 | 4/1992 | Wall et al. . |
| 5,122,383 | 6/1992 | Heiber et al. ............ 424/449 |
| 5,126,351 | 6/1992 | Luzzio et al. . |
| 5,180,722 | 1/1993 | Wall et al. . |
| 5,225,404 | 7/1993 | Giovanella et al. . |
| 5,352,789 | 10/1994 | Hinz . |
| 5,391,745 | 2/1995 | Danishefsky et al. . |
| 5,466,047 | 11/1995 | Danishefsky et al. . |
| 5,505,958 | 4/1996 | Bello et al. ............. 424/449 |
| 5,525,731 | 6/1996 | Danishefsky et al. . |
| 5,541,327 | 7/1996 | Danishefsky et al. . |
| 5,552,154 | 9/1996 | Giovanella et al. . |
| 5,613,958 | 3/1997 | Kochinke et al. ............ 604/307 |
| 5,652,244 | 7/1997 | Giovanella et al. . |
| 5,843,468 | 12/1998 | Burkoth et al. ............ 424/448 |

OTHER PUBLICATIONS

Giovanella et al., *Science*, vol. 246, pp. 1046–1048, Nov. 24, 1989.

Adamovics, *Chem. Absts.* vol. 92, entry 59061 (1980).

Yakult, *Chem. Absts.*, vol. 101, entry 91319d (1984).

Yakult, *Chem. Absts.*, vol. 101, entry 913222 (1984).

Wu, *Chem. Absts.*, vol. 123, entry 52308 (1995).

Wu et al., *Phytochemistry*, vol. 39, No. 2, pp. 383–385, May 1995.

Wall and Wani, *Nat. Prod. and Drug Dev.*, Munksgaard, Copenhagen, 1984.

Adamovics, *Phytochemistry*, vol. 18, pp. 1085–1086, 1979.

Database WPI (Week 8946); AN 89–335912; pp. 1–2, Derwent Publications Ltd., London, GB; XP002033248; Abstract of JP 01 249 777a (Yakult Honsha K.K.) Oct. 5, 1989.

Database WPI (Week 9347); AN 93–374594; pp. 1–2, Derwent Publications Ltd., London, GB; XP00203349; Abstract of JP 05 279 370 A (Daiichi Pharm. Co., Ltd. & Hakult Honsha K.K.) Oct. 26, 1993.

Database WPI (Week 8945); AN 89–329502; pp. 1–2; Derwent Publications Ltd., London, GB; XP002033250; Abstract of JP 01 246 287 A (Yakult Honsha K.K.) Oct. 2 1989.

Wall et al., "Plant Antitumor Agents. 30, Synthesis and Structure Activity of Novel Camptothecin Analogs," *J. Med. Chem.*, vol. 36, No. 18, pp. 2689–2700, 1993.

International Search Report for PCT/US97/01728 dated Jul. 15, 1997.

METHODS OF TREATING CANCER USING THESE DERIVATIVES

This application is a continuation of Ser. No. 09/030,357 Feb. 25, 1998, U.S. Pat. No. 5,968,943 and a continuation-in-part U.S. patent application Ser. No. 08/594,235 filed Jan. 30, 1996, now U.S. Pat. No. 5,731,316 and PCT Application No. PCT/US97/01728 filed Jan. 29, 1997, both of which are incorporated by reference herein

FIELD OF THE INVENTION

The present invention is directed to derivatives of camptothecin, preferably having low toxicity, and to the use of these derivatives for cancer treatment. The disclosures of all documents referred to in this application are incorporated herein in whole by reference.

BACKGROUND OF THE INVENTION

Camptothecin, a cytotoxic alkaloid first isolated from the wood and bark of Camptotheca Acuminata (Nyssaceae) by Wall and his coworkers (J. Am. Chem. Soc. 88, 3888, 1966), was shown to have antitumor activity against the mouse leukemia L 1210 system. The structure of camptothecin, an alkaloid which has a commonly occurring indole alkaloid group (Heckendorf et al, J Org. Chem. 41, 2045, 1976), is shown below as Formula (X).

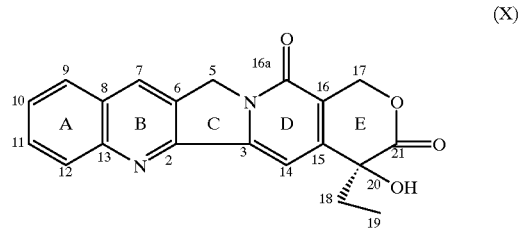

This compound has a pentacyclic ring system with only one asymmetrical center in ring E with a 20(S)-configuration. The pentacyclic ring system includes a pyrrolo [3, 4—b] quinoline moiety (rings A, B and C), a conjugated pyridone (ring D), and a six-membered lactone (ring E) with an α-hydroxyl group. Camptothecin was of great interest from the time of its initial isolation due to its noteworthy activity in the mouse leukemia L 1210 system. Earlier data for the antitumor activity of camptothecin were obtained by employing experimentally transplanted malignancies such as leukemia L 1210 in mice, or Walker 256 tumor in rats (Chem. Rev. 23, 385, 1973, Cancer Treat. Rep. 60, 1007, 1967). Subsequent clinical studies showed that this compound was not usable as an anticancer agent in vivo due to its high toxicity. Camptothecin itself is insoluble in water. Therefore, camptothecin was evaluated clinically as a water-soluble sodium carboxylate salt in the early times. This form of camptothecin produced severe toxicity and seemed devoid of anticancer activity (Gottlieb et al, Cancer Chemother. Rep. 54, 461, 1970, and 56, 103, 1972, Muggia et al, Cancer Chemother. Rep. 56, 515, 1972, Moertel et al, Cancer Chemother. Rep. 56, 95, 1972, and Schaeppi et al, Cancer Chemother. Rep. 5:25, 1974). These results caused the discontinuation of phase II trials. Continued evaluation of this agent showed that the sodium carboxylate salt is only 10% as potent as the native camptothecin with the closed lactone ring intact (Wall et al, In International Symposium on Biochemistry And Physiology of The Alkaloids, Mothes et al, eds, Academie—Verlag, Berlin, 77, 1969, Giovanella et al, Cancer res. 51, 3052, 1991). In addition, important parameters for antitumor activity in the camptothecin family have been established (Wall et al, Ann. Rev., Pharmacol Toxicol. 17, 117, 1977). These results indicate that intact lactone ring E and α—hydroxyl group are essential for antitumor activity.

In 1989, Giovanella et al. found that some of the non-water soluble derivatives of camptothecin have high antitumor activity against xenograft of human tumors (Giovanella et al., Science, 246, 1046, 1989). It has also been shown that administration of camptothecin with closed lactone ring is superior to injections of water-soluble carboxylate salt (Giovanella et al, Cancer Res., 51, 3052, 1991). These findings further confirmed the importance of the intact lactone ring.

Clearly, there is a need to modify 20(S) amptothecin ("CPT") to enable the lactone form to stay longer in the body while retaining the structural elements (i.e. 20hydroxyl and lactone ring E) which are essential for its antitumor activity.

Ring opening of CPT leads to much more potent anticancer activity in mice than in humans. In effect, CPT administered intramuscularly ("i.m."), subcutaneously ("s.c."), and intrastomach ("i.s.") has proved to be a very potent anticancer agent against human tumors in mice, i.e., when growing as xenotransplants in nude mice (Giovanella et al, Cancer Res. 51:3052, 1991). However, when tumors were treated with CPT in humans, a lower degree of anticancer activity in humans, than in mice, was exhibited (Stehlin et al., In Camptothecins: New Anticancer Agents, 1995, CRC Press, pp. 59–65).

The same phenomenon was observed with other CPT derivatives. In mice, 9-nitrocamptothecin ("9NC") has proven to be 2–3 times more potent than CPT against human tumor xenografts causing the total eradication of all the human malignancies treated (Pantazis et al., Cancer Res. 53:1577, 1993; Pantazis et al., Int. J. Cancer 53:863, 1995).

Pharmacological studies demonstrated that the majority (57%) of the 9NC drug present in the plasma after i.s. administration is in the closed lactone form (FIG. 3). Pharmacological studies on the plasma levels of 9NC after oral administration to Phase I clinical trial patients demonstrate that, on average, only ~3% of the drug present is in the closed lactone form (FIGS. 4 and 5).

In perfect agreement with such findings, the clinical responses in this group of patients, although higher than those obtained with CPI are still a far cry below the results obtained in mice (32/32 complete tumor regressions in mice versus 2/32 in humans). Clearly, again there is a pressing need for a modification which will slow and delay the lactone ring opening upon its entrance into the blood circulation.

A number of attempts have made to provide more active derivatives of camptothecin, but none of these compounds has been disclosed to be able to delay the opening of the lactone ring E.

SUMMARY OF THE INVENTION

Accordingly, it is an object of the present invention to provide new CPT derivatives which are effective antitumor agents, preferably useful for the oral and intramuscular routes of drug administration.

It is another object of the present invention to provide new active CPT derivatives which sustain the opening of the lactone ring E, which makes the antitumor activity last longer than its mother analog, CPT.

It is still another object of the present invention to provide new CPT derivatives which retain significant antitumor activity as does the mother compound, CPT, and have much lower toxicity than its mother compound.

It is still another object of the present invention to provide new CPT derivatives possessing good absorbability in the living body.

It is a further object of the present invention to provide new CPT derivatives which retain the lactone ring E and the 20-hydroxyl group intact, which are important for antitumor activity.

It is still a further object of the present invention to provide a method for preparing CPT derivatives.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a compound of formula (I):

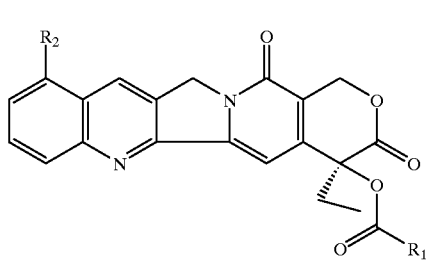

wherein $R_2$ is H or $NO_2$, and $R_1$ is a $C_2$–$C_4$ alkyl group, a $C_6$–$C_{15}$ alkyl group, a $C_3$–$C_8$ cycloalkyl group, a $C_2$–$C_{15}$ alkenyl group, or an epoxy group when $R_2$ is H; and $R_1$ is a $C_1$–$C_{15}$ alkyl group, a $C_1$–$C_{15}$ alkenyl group, a $C_3$–$C_8$ cycloalkyl group, or an epoxy group when $R_2$ is $NO_2$.

The invention also relates to a method for treating malignant tumors in a mammal and comprises administering an effective amount of one or more of the above compounds.

DETAILED DESCRIPTION OF THE INVENTION

The metabolism studies of camptothecin in human plasma carried out in the laboratory showed that the only metabolite detected is the ring-opened sodium carboxylate salt which is toxic and inactive. The measurement of pharmacokinetics for CPT in human plasma indicates that the half-life time of the drug with lactone intact is 30 min. These results implies that the drug will lose 90% of its activity and produce a lot of toxicities in very short time after the patients take it.

Figure 1:
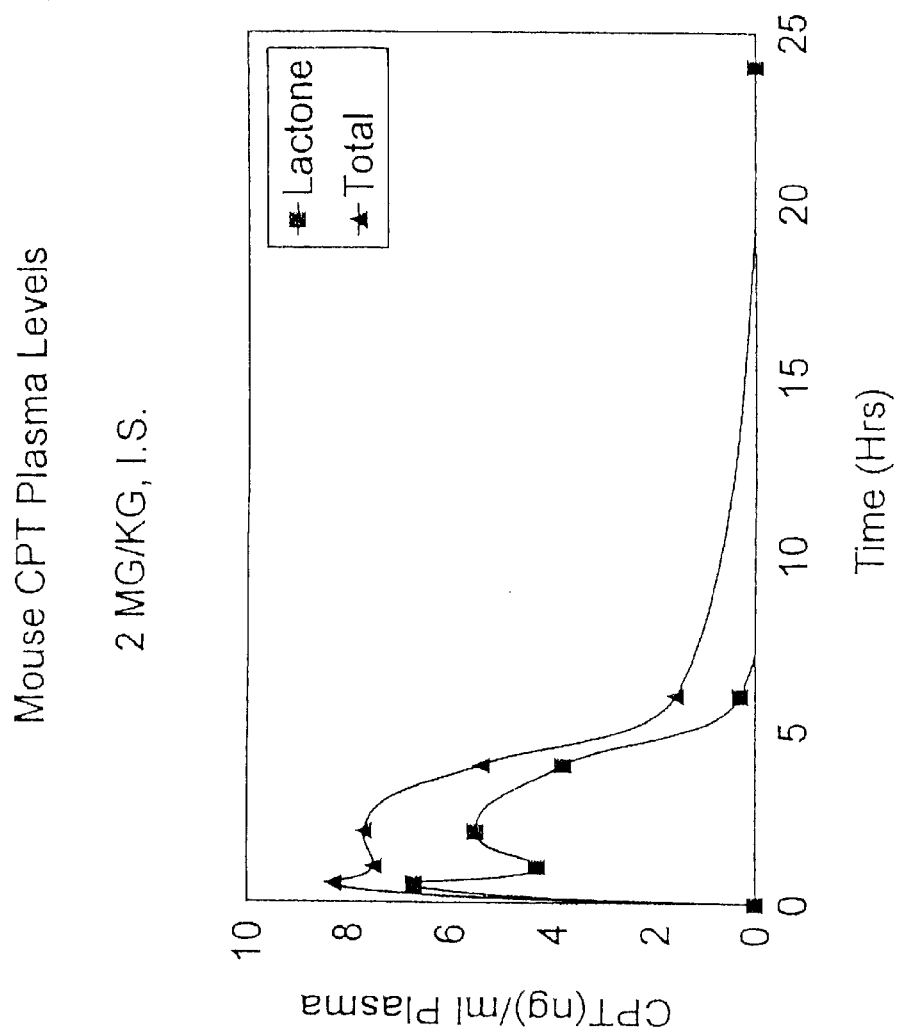
FIG. 1 is a graph showing the presence of CPT in the closed lactone form in mice after intrastomach administration.
Figure 2:
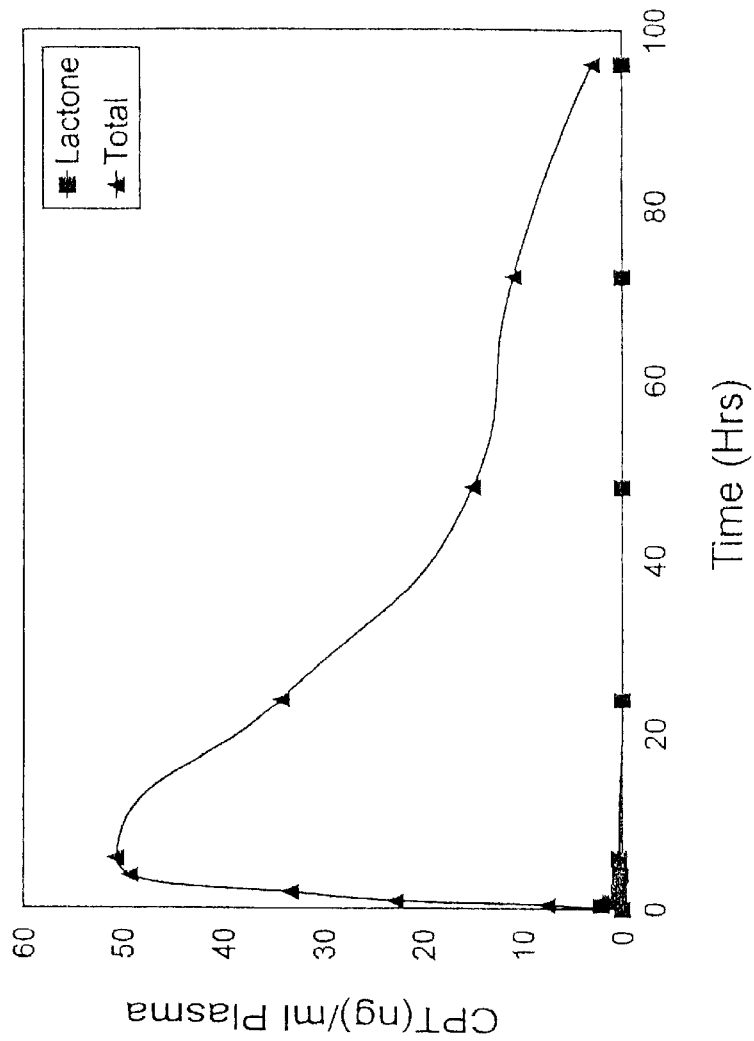
FIG. 2 is a graph showing the amount of CPT and its closed lactone form in a human after oral administration.
Figure 3:
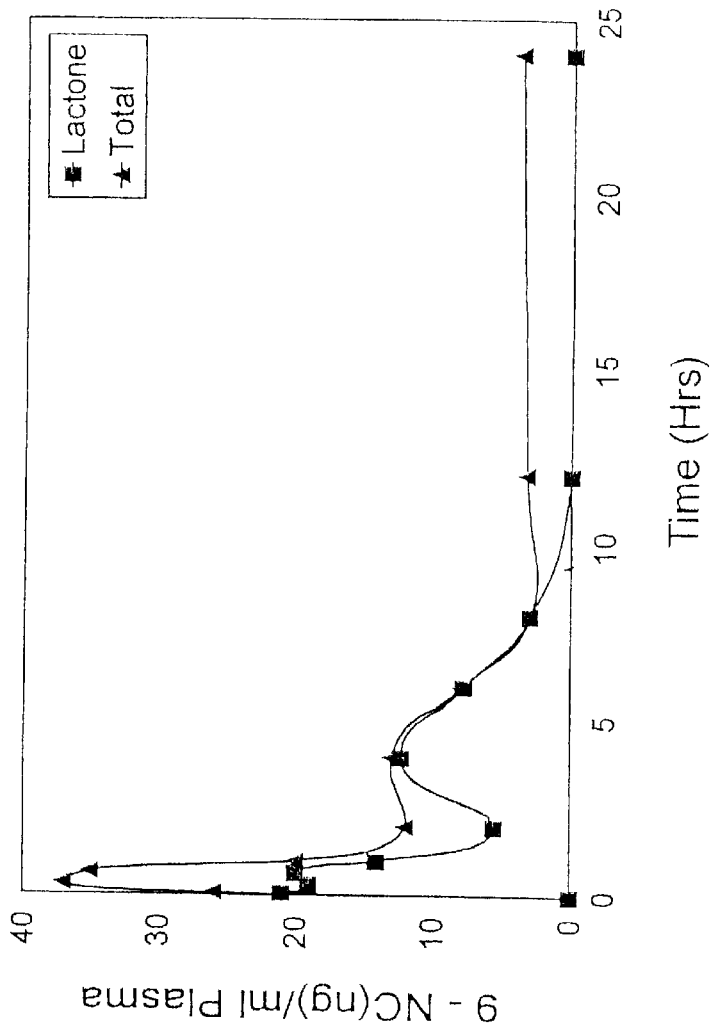
FIG. 3 is a graph of the amount of 9-nitrocamptothecin and its closed lactone ring form in a mouse after oral administration.

Comparative pharmacological studies in mice and humans have demonstrated that in mice the majority of the CPT present in the plasma after intrastomach administration is of the closed lactone form (FIG. 1), approximately 54% of the area under the curve. In humans, on the contrary, only about 0.4% of the area under the curve after oral administration of CPT is in the form of closed ring lactone (FIG. 2).

This difference between a mouse and a human is caused by the fact that although the blood pH of the mouse and human are the same, i.e., 7.4, the human albumin, which catalyzes the conversion of CPT into its sodium salt is ~100 times more efficient in this process than mouse albumin (Mi and Burke, Biochem. 33:12540, 1994).

According to the present invention, CPT is converted into more lipo-soluble molecules, hereinafter, also called prodrugs. When taken orally by patients, the prodrugs are rapidly introduced into the bloodstream of the patients and are readily converted to the parent compound in the body.

Conversion of the prodrugs to the mother compound, CPT, is mediated by a group of enzymes called esterases present in the blood of many animals, including humans. Since the prodrugs are rapidly distributed throughout the body in a short period of time after delivery, these compounds exist at a very low concentration at the time they undergo enzymatic hydrolysis by which the mother camptothecin is released, which prevents CPT from precipitating in the bloodstream.

In an attempt to synthesize new CPT derivatives with extremely reduced toxicity, while maintaining the inherent antitumor activity, the present inventors have performed an acylation reaction of camptothecin with various organic acids, organic acid chlorides, and organic acid anhydrides. A number of new camptothecin derivatives have been obtained. They are characterized by the formula I as shown below:

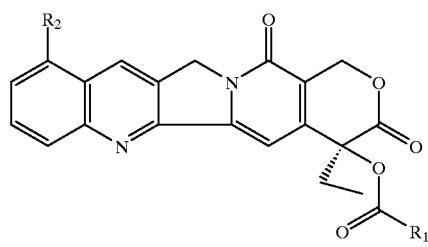

(I)

wherein $R_2$ is H or $NO_2$. $R_1$ in formula I represents a $C_2$–$C_4$ alkyl group, a $C_6$–$C_{15}$ alkyl group, a $C_3$–$C_{15}$ cycloalkyl group, a $C_2$–$C_{15}$ alkenyl group or a $C_2$–$C_{15}$ epoxy group when $R_2$ is H. When $R_2$ is $NO_2$, $R_1$ is a $C_1$–$C_{15}$ alkyl group, a $C_3$–$C_8$ cycloalkyl group, a $C_2$–$C_{15}$ alkenyl group or a $C_2$–$C_{15}$ epoxy group. Preferably, when $R_2$ is H, $R_1$ is $CH_2CH_3$; $CH_2CH_2CH_3$; $CH_2CH_2CH_2CH_3$; $CH_2CH_2CH_2CH_2CH_3$; $CH_2CH_2CH_2CH_2CH_2CH_2CH_2CH_3$; $CH=CH_2$; $CH=CHCH_3$(trans); or

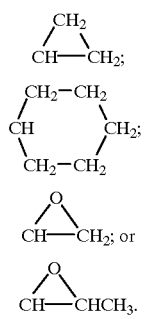

Also, when $R_2$ is $NO_2$, $R_1$ is preferably $CH_3$; $CH_2CH_3$; or $CH_2CH_2CH_3$; $CH=CH_3$; $CH=CHCH_3$(trans);

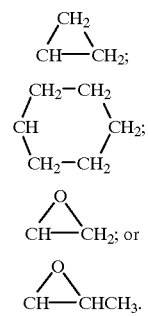

The analogues of 9-nitroccmptothecins are prepared by the acylation of 9-nitrocamptothecin with organic anhydrides. All epoxy derivatives can be prepared by the reactions of the corresponding alkenyl esters of the present invention with m-chloroperoxy benzoic acid in benzene at room temperature.

Figure 6:
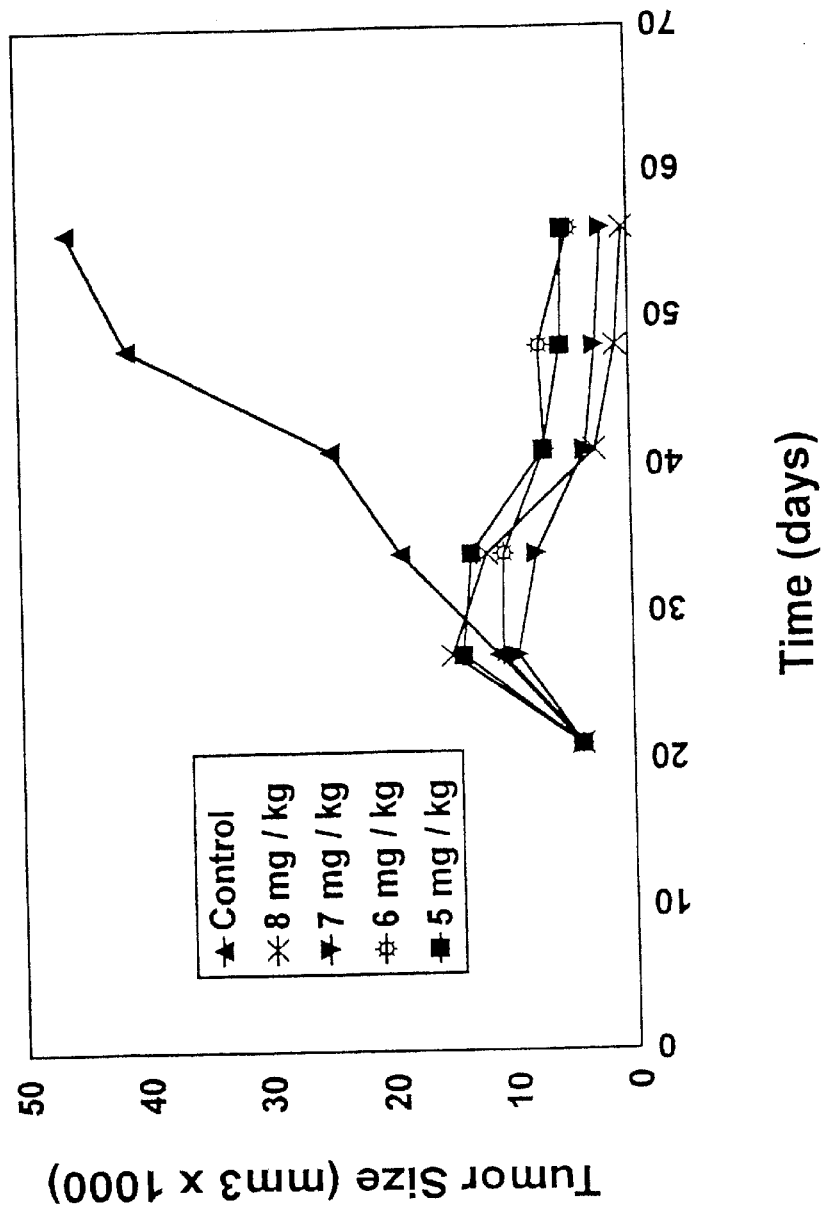
FIG. 6 is a graph representing the antitumor activity of camptothecin 20(S) propionate in an implanted human breast carcinoma CLO in nude mice.

The preferred derivatives display significant antitumor activity with much lower toxicity than their parent camptothecin, CPT. The animal experimental data for these new derivatives were collected. Camptothecin 20(S) propionate (where $R_1$ is ethyl and $R_2$ is H) is designated as Prodrug 2 and taken as a example to disclose some in vivo experimental data. FIG. 6 represents the antitumor activity of this compound in different doses against the implanted human breast carcinoma (CLO) in nude mice. Table 1 represents the toxicity of this compound against nude mice with different doses. The change of body weight of mice is recorded with the time. There were no losses of mice body weights during the test time period.

TABLE 1

The Changes of Body Weights of Mice during The Test Time Period

| Dose (mg/kg) | Time (days)/Body weight (gms) | | | | | |
|---|---|---|---|---|---|---|
| Control | 21/32.7 | 27/33.5 | 34/34.4 | 41/35.2 | 48/35.0 | 56/36.7 |
| 5 | 21/33 | 27/33.7 | 34/34.3 | 41/33.5 | 48/32.9 | 56/33.2 |
| 6 | 21/32.9 | 27/33.4 | 34/33.8 | 41/33.5 | 48/34.0 | 56/32.2 |
| 7 | 21/30.8 | 27/31.7 | 34/30.6 | 41/31.1 | 48/31.6 | 56/31.5 |
| 8 | 21/32.9 | 27/34.1 | 34/34.0 | 41/33.4 | 48/33.9 | 56/33.2 |

The measurement of pharmacokinetics for Prodrug 2, camptothecin 20(S) propionate, shows that the lactone ring remained intact in human plasma much longer than its mother camptothecin, CPT. Table 2 represents this result.

TABLE 2

| Comparison of Lactone % of 20(S) Propionate and Lactone % of Camptothecin in Human Plasma | | | | | |
|---|---|---|---|---|---|
| Time (Hr.) | 0 | 1 | 2 | 4 | 6 |
| Lactone % for prodrug 2 | 100 | 86 | 77 | 68 | 56 |
| Lactone % for camptothecin | 100 | 12 | 0.5 | 0 | 0 |

Figure 7:
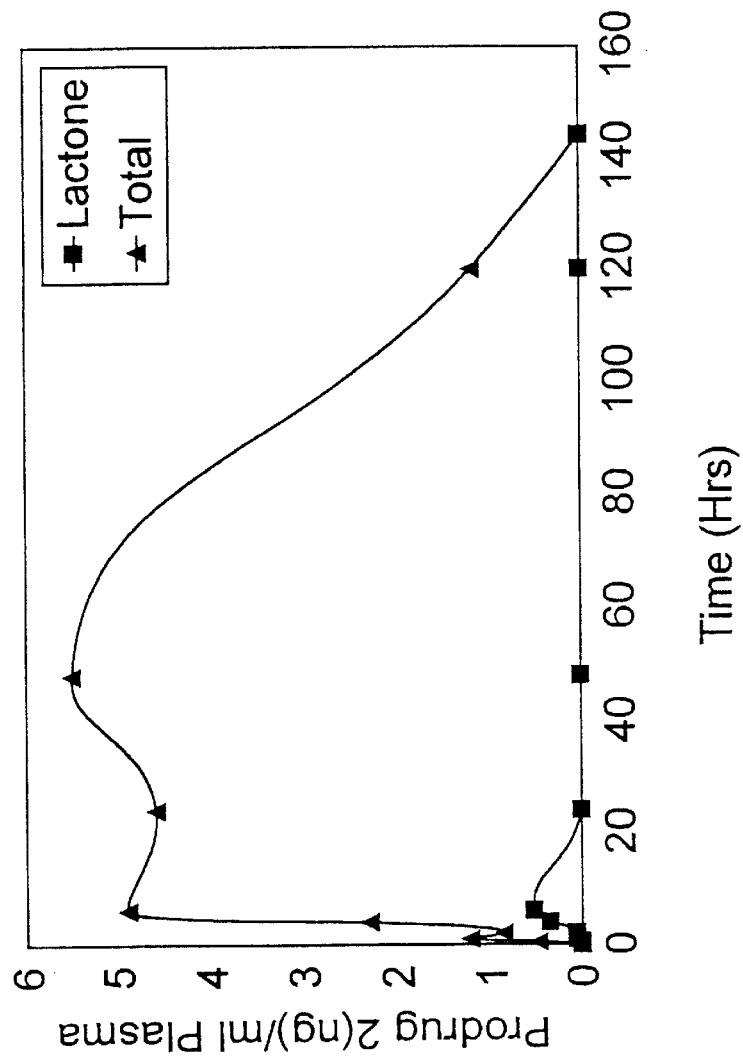
FIG. 7 is a graph showing the presence of camptothecin 20(S) propionate and its closed lactone ring form in human plasma after oral administration.

As reflected in the tables, augmenting the biological life of the closed lactone ring has been achieved. As shown in FIG. 2, the % of CPT present as closed lactone form in human blood after oral administration is 0.4%. Its analogue, 20-(S) propionate, under similar conditions reaches 2.8% (FIG. 7), an increase of sevenfold. This compound exhibits antitumor activity against human tumor xenografts and an exceptional lack of toxicity, even at enormous doses in mice.

Figure 4:
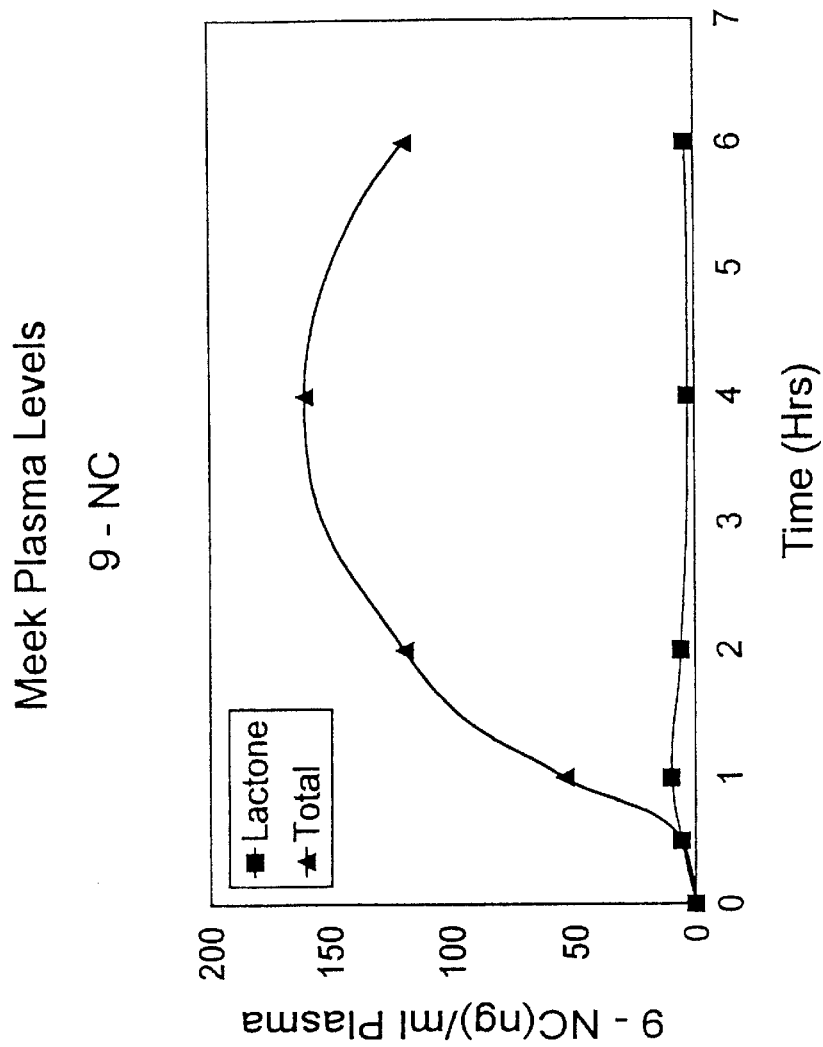
FIGS. 4 and 5 show the amount of 9-nitrocamptothecin and its closed lactone ring in clinical trial patients who received the dosage by oral administration.
Figure 5:
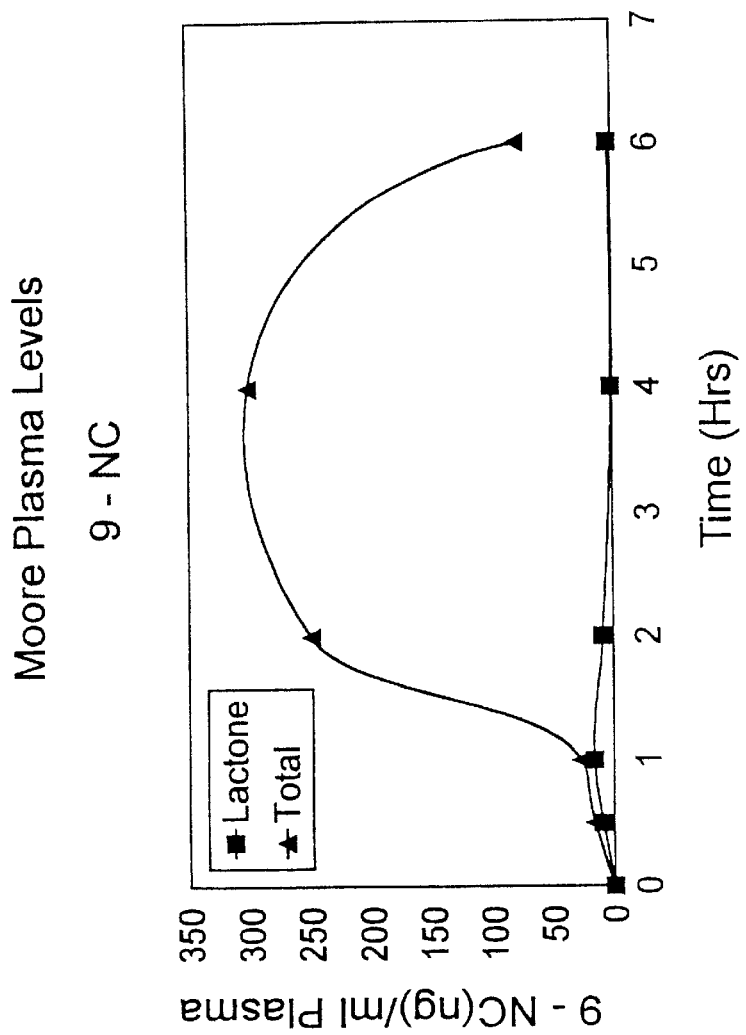
Figure 8:
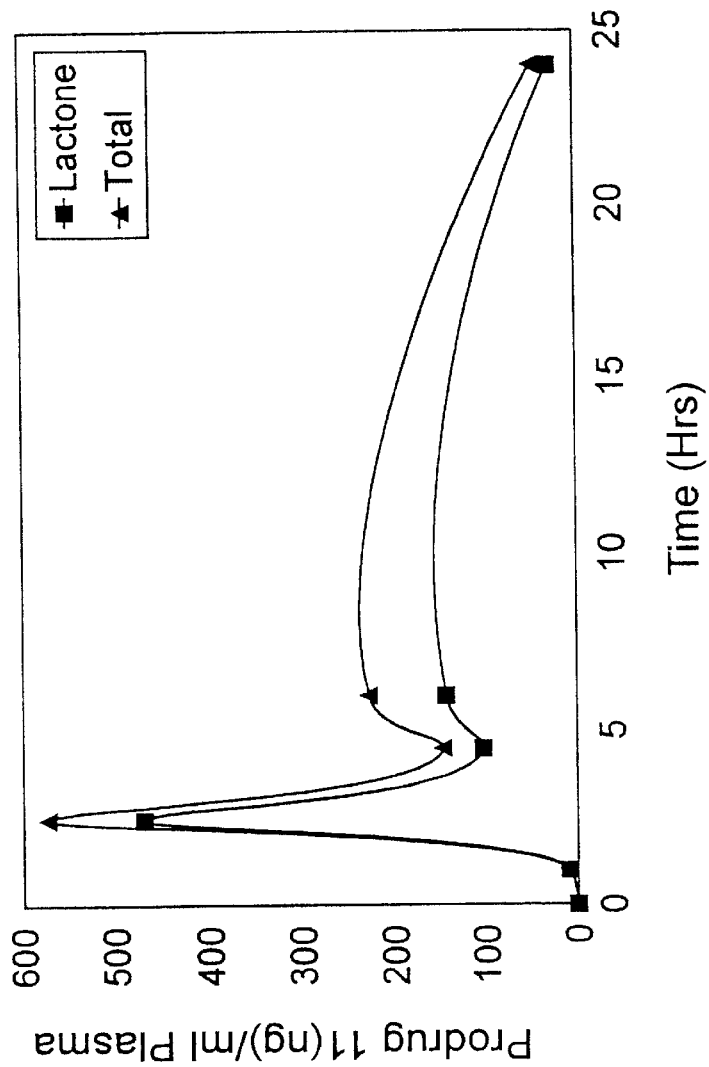
FIG. 8 is a graph showing the presence of 9-nitrocamptothecin-20-O-propionate in a patient who received the compound orally.

Even more striking are the results obtained with 9NC. As shown in FIGS. 4 and 5, after oral administration of this compound, only ~3% of it is present in the plasma as lactone. When its analogue, Prodrug 11 of the present invention, (where $R_1$ is ethyl and $R_2$ is $NO_2$) was prepared and administered orally to a patient, the lactone form constituted 68.7% of the total, an increase of more than twentyfold (FIG. 8). This compound also exhibited antitumor activity against xenografts of human tumors in nude mice, even higher than the camptothecin analogue, Prodrug 2, where $R_1$ is ethyl and $R_2$ is H and with very low toxicity.

The compounds of the present invention can be made in the following manner. 20(S)-camptothecin or 9-nitrocamptothecin can be reacted with organic anhydrides in pyridine for example. In particular, the anhydride is mixed with pyridine in about a 1:1 ratio to provide a homogeneous solution to which the 20(S)-camptothecin or 9-nitrocamptothecin is added all at once. The mixture is stirred under atmosphere for 24 to 48 hours. At the end of the reaction time, the mixture is poured onto a certain amount of petroleum ether while stirring. The product, precipitated from petroleum ether, is collected by filtration and washed with petroleum ether several times. The purity of the product by this procedure is usually 98% (analyzed by HPLC). This procedure is applicable to all of the compounds of the present invention except where $R_1$ is $C_7$–$C_{15}$ alkyl or alkenyl, or an epoxy group in Formula (I). The derivative where $R_1$ is a $C_7$–$C_{15}$ alkyl is obtained by the reaction of camptothecin with nonanoyl chloride in methylene chloride under reflux. The derivative where $R_1$ contains an epoxy moiety is obtained by epoxidation of the compound of the present invention, where $R_1$ is an alkenyl group in Formula (I).

The compounds of the present invention are effective in treating malignant tumors in a mammal. The compounds of the present invention can be administered in any fashion known to those skilled in the art. Preferably, the compounds are administered intramuscularly, orally, or transdermally.

As used herein, the term "malignant tumor" is intended to encompass all forms of human carcinomas, sarcomas and melanomas which occur in the poorly differentiated, moderately differentiated, and well differentiated forms.

In treating or retarding malignant tumors in mammals in accordance with the present invention, the aforedescribed CPT derivatives of the present invention are administered by means known to those skilled in the art, and are preferably administered intramuscularly, transdermally, or orally, using commonly known methods, for example, gelatin capsules for oral administration, as well as formulations such as microsuspensions in lipid and in lipid-like emulsions (e.g.— Intralipid 20, cottonseed oil and peanut oil) for intramuscular administration and inclusion in cholesterol pellets for subcutaneous long-term administration.

As used herein, an "effective amount" of CPT derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on $mg/M^2$ of body surface) is described by E. J. Freireich et al., *Cancer Chemother. Rep.*, 50(4):219 (1966). Body surface area may be approximately determined from the height and weight of an individual (see, e.g., *Scientific Tables*, Geigy Pharmaceuticals, Ardsley, N.Y. pp. 537–538 (1970). An effective amount of the camptothecin compounds in the present invention can range from about 12.5 to about 31.3 $mg/m^2$ of body surface per day.

The preferred effective amounts or dosages of CPT derivatives or prodrugs of the present invention in mice are about 1 to about 4 mg Prodrug/kg of body weight twice a week for an intramuscular route and about 0.75 to about 1.5 mg Prodrug/kg/day for the oral route. Effective amounts or dosages of CPT derivatives or Prodrugs of the present invention in mice are, for instance, about 1.5 mg/kg/week to about 10 mg/kg/week of the Prodrug for the transdermal route. For all of the administering routes, the exact timing of administration of the dosages can be varied to achieve optimal results. Generally, when using Intralipid 20 as the carrier for the CPT derivative, the actual dosage of CPT derivative reaching the patient will be less. This is due to some loss of the CPT derivative on the walls of the syringes, needles and preparation vessels, which is prevalent with the Intralipid 20 suspension. When a carrier, such as cottonseed oil is used, this above-described loss is not so prevalent because the CPT derivative does not adhere as much to the surfaces of syringes, etc . . . For instance and preferably, it has been found that generally about 2.5 mg Prodrug/kg of body weight twice per week using cottonseed oil, administered by an intramuscular route, will deliver the same amount to the patient as 4.0 mg Prodrug/kg of body weight twice per week using Intralipid 20 as a carrier. Generally, about 1 mg to about 4 mg of CPT derivative is added to about 0.1 ml to about 1 ml of carrier.

Another important feature of the method provided by the present invention relates to the relatively low or no apparent overall toxicity of the CPT derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity. In one of the examples which follow, the overall toxicity of the camptothecin compounds of the present invention was evaluated.

The compounds of the present invention may be administered in combination with pharmaceutically acceptable carriers or diluents, such as Intralipid 10 or 20 or natural oils, or other suitable emulsifiers for lipophilic compounds.

Another method of administering the compounds of the present invention is by a transdermal or transcutaneous route. One example of such an embodiment is the use of a patch. In particular, a patch can be prepared with a fine suspension of a compound disclosed in the present application in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the CPT derivative of the present invention in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

The present invention will be further clarified by the following example, which is intended to be purely exemplary of the present invention.

EXAMPLES

All glassware referenced in the examples was baked at 80–100° C. for a minimum of 2 hours before being used. Melting points were obtained with a MEL-TEMP melting point apparatus and were uncorrected. The $^1$H and $^{13}$C NMR spectra were obtained at 270.05 $_{MHz}$ with a JEOL GX-270 WB NMR spectrometer. Chemical shifts are reported in parts per million (δ scale), employing tetramethylsilane as an internal standard. In reporting the NMR data, the following abbreviations are used: coupling constants in Hertz (J), singlet (s), doublet (d), triplet (t), broad singlet (brs), multiplet (m), and etc. Mass Spectra were recorded using a VG ZAB—SEQ mass spectrometer (VG Analytical Co., England) with a resolution of 10000. The numbering system used to depict NMR for camptothecin portion is shown in formula (X). The numbering for the side chain is shown as below:

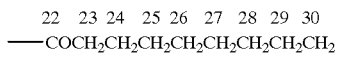

Example 1-Camptothecin 20-O-propionate

In a 100 ml round—bottomed flask were mixed 25 ml propionic acid anhydride and 20 ml pyridine. A homogeneous solution was obtained after shaking for 30 s. To this solution, 2.0 g of starting camptothecin was suspended. The mixture was stirred at 40±5° C. for 48 h. After cooling to room temperature, the reaction mixture was poured onto 400 ml petroleum ether while stirring. The product precipitated from petroleum ether was collected by filtration and washed with 150 ml petroleum ether (50 ml×3). After drying under air for 1 h, a white powder, 2.17 g, was obtained. The purity of the product which was measured by HPLC was 98%. Yield 94%, mp 250–252° C. (dec.). $^1$HNMR in CDCl$_3$: 0.98 (3H, t, J=7.5 Hz, 19-methyl protons), 1.17 (3H, t, J 7.51 Hz, 24-methyl protons), 2.12–2.34 (2H, m, 18-methylene protons), 2.48–2.58 (2H, m, 23-methylene protons), 5.29 (2H, s, 5-methylene protons), 5.39–5.72 (2H, dd, J=17.12, 17.12 Hz, 17-methylene protons), 7.23 (1H, s, 14-H), 7.68 (1H, t, J=6.96 Hz, 10-H), 7.84 (1H, t, J=6.96 Hz, 11-H), 7.95 (1H, d, J=8.43 Hz, 9-H), 8.23 (1H, d, J=8.06 Hz, 12-H), 8.40(1H, s, 7-H); $^1$H NMR in TFA: 1.18(3H,t,J=7.5 Hz, 19-methyl protons), 1.32 (3H, t, J=7.30 Hz, 24-methyl protons), 2.30–2.80 (4H, m, 18- and 23-methylene groups), 5.60–6.10 (4H, s+dd, s at 5.86 for 5-methylene protons, dd with J=18.96, 18.32 Hz for 17-methylene protons), 7.99 (1H, s, 14-H), 8.19 (1H, t, J=8.06 Hz, 10-H), 8.20–8.46 (2H, m, 9-H and 11-H), 8.54 (1H, d, J=8.79 Hz, 12-H), 9.43 (IH, s, 7-H); $^{13}$C NMR (TFA): 7.42 (C19), 8.55 (C24), 28.61 (C18), 33.07 (C23), 53.14 (C5), 68.77 (C17), 78.31 (C20), 105.68, 113.19, 117.35, 125.87, 131.23, 131.36, 132.59, 133.40, 139.30, 139.89, 140.78, 144.62, 147.00, 149.43 (C2, C3, C6–C16, C16a), 172.50, 179.76 (C21, C22); mass m/e (relative intensity): 405 [(M+H)+, 100%], 404 (M+, 15%), 331 [(M—CH$_3$CH$_2$COO), 17%], 317 [(M—C$_2$H$_5$COO—CH$_3$+H), 10%], 303 [(M—C$_2$H$_5$COO—CO), 15%], 287 [(M—C$_2$H$_5$COO—CO2), 9%], 261(9%).

Example 2—Campothecin 20-O-butyrate

Using 20 ml butyric anhydride, 18 ml pyridine, and 1.61 g camptothecin, the reaction is carried out in the same manner as in Example 1 whereby 1.77 g of the title compound was obtained as a brownish powder, yield 92%, mp 225–227° C. (dec.). $^1$H NMR in CDCl$_3$: 0.98 (6H, t, J=7.51 Hz, 19- and 25-methyl groups), 1.65–1.74 (2H, m, 24-methylene protons), 2.14–2.30 (2H, m, 18-methylene protons), 2.44–2.51 (2H, m, 23-methylene protons), 5.29 (2H, s, 5-methylene protons), 5.38–5.71 (2H, dd, J=17.59, 17.59 Hz, 17-methylene protons), 7.23 (1H, s, 14-H), 7.68 (1H, t, J=8.06 Hz, 10-H), 7.84 (1H, t, J=7.96 Hz, 11-H), 7.95 (1H, d,J=6.96 Hz, 9-H), 8.23 (1H, d, J=8.06 Hz, 12-H), 8.40 (1H, s, 7-H); $^1$H NMR in TFA: 0.75–1.15 (6H, m, 19- and 25-methyl groups), 1.70–1.80 (2H, m, 24-methylene protons), 2.10–2.80 (4H, m, 18- and 23-methylene groups), 5.50–6.00 (4H, s+dd, s at 5.73 for 5-methylene protons, dd for 17-methylene protons), 7.86 (1H, s, 14-H), 8.05 (1H, s, 10-H), 8.30 (2H, brs, 9-H and 11-H), 8.40 (1H, s, 12-H), 9.30 (1H, s, 7-H); $^{13}$C NMR (TFA): 7.23 (C19), 13.20 (C25), 19.20 (C24), 32.91 (C18), 36.91 (C23), 52.96 (C5), 68.58 (C17), 78.00 (C20), 105.56, 113.40, 113.50, 117.00, 117.10, 131.00, 132.40, 133.16, 139.06, 139.15, 140.00, 144.36, 146.90, 149.40 (C2, C3, C6–C16, C16a), 172.50, 178.00 (C12, C22); mass m/e (relative intensity): 419 [(M+H)+, 100%], 331 [(M—C$_3$H$_7$COO), 17%], 303 [(M—C$_3$H$_7$COO—CO), 13%], 287 [(M—C$_3$H$_7$COO—CO$_2$), 8%], 273 (2%), 261(3%).

Example 3-Camptothecin 20-O-valerate

Using 15 ml valeric anhydride, 14 ml pyridine, and 1.51 g starting camptothecin, the reaction was carried out in the same manner as in Example 1 whereby 1.68 g of the title compound was obtained as a gray—white powder, yield 90%, mp 265° C. (dec.). $^1$H NMR in CDCl$_3$: 0.92 (3H, t, J=7.33 Hz, 26-methyl protons), 0.98 (3H, t, J=7.51, 19-methyl protons), 1.37–2.00 (4H, m, 24- and 25-methylene protons), 2.10–2.28 (2H, m, 18-methylene protons), 2.46–2.53 (2H, m, 23-methylene protons), 5.30 (2H, s, 5-methylene protons), 5.38–5.71 (2H, dd, J=17.22, 17.21 Hz, 17-methylene protons), 7.23 (1H, s, 14-H), 7.70 (1H, t, J=6.96 Hz, 10-H), 7.82 (1H, t, J=6.96 Hz, 11-H), 7.95 (1H, d, J=7.32 Hz, 9-H), 8.22 (1H, d, J=8.42 Hz, 12-H), 8.40 (1H, s, 7-H); $^1$H NMR In TFA: 0.83 (3H, brs, 26-methyl protons), 0.99 (3H, brs, 19-methyl protons), 1.32 (2H, m, 25-methylene protons), 1.60 (2H, m, 24-methylene protons), 2.19–2.58 (4H, m, 18- and 23-methylene protons), 5.49–5.82 (4H, s+dd, s at 5.67 for 5-methylene protons, dd with J=17.58, 18.68 Hz for 17-methylene protons), 7.80 (1H, s, 14-H), 7.99 (1H, s, 10-H), 8.23 (2H, brs, 9-H and 11-H), 8.33 (1H, s, 12-H), 9.24 (1H, s, 7-H); $^{13}$C NMR (TFA): 4.48 (C26), 10.37 (C19), 20.23 (C24), 24.98 (C25), 30.15 (C18), 32.03 (C23), 50.20 (C5), 65.82 (C17), 75.36 (C20), 102.84, 109.89, 110.24, 114.06, 114.39, 128.25, 128.39, 129.65, 130.41, 136.30, 137.00, 141.62, 148.57, 149.28 (C2, C3, C6–C16, C16a), 169.00, 176.80 (C21, C22); mass m/e (relative intensity): 433 [(M+H)$^+$, 100%], 331, [(M—C$_4$H$_9$COO), 17%], 303 [(M—C$_4$H$_9$COO—CO), 13%], 287 [(M—C$_4$H$_9$COO—CO$_2$), 7%], 273 (2%), 261 (4%).

Example 4-Camptothecin 20-O-hepotanoate

Using 15 ml heptanoic anhydrides, 13 ml pyridine, and 1.55 g starting camptothecin, the reaction was carried out in the same manner as in Example 1 whereby 2.0 g of the title compound was obtained as a gray—white powder, yield 98%, mp 270° C. (deformed at 210° C.). $^1$H NMR in CDCl$_3$: 0.82 (3H, t, J=7.51 Hz, 28-methyl protons), 0.98 (3H, t, J=7.01 Hz, 19-methyl protons), 1.20–1.80 (8H, m, 24-, 25-, 26-, and 27-methylene protons), 2.10–2.30 (2H, m, 18-methylene protons), 2.40–2.60 (2H, m, 23-methylene protons), 5.29 (2H, s, 5-methylene protons), 5.38–5.72 (2H, dd, J=17.69, 17.22 Hz, 17-methylene protons), 7.23 (1H, s, 14-H), 7.68 (1H, t, J=7.30 Hz, 10-H), 7.84 (1H, t, J=7.42 Hz, 11-H), 7.95 (1H, d, J=8.06 Hz, 9-H), 8.22 (1H, d, J=8.32 Hz, 12-H), 8.40(1H, s, 7-H); $^1$H NMR in TFA: 0.74 (3H, s, 28-methyl protons), 0.99 (3H, s, 19-methyl protons), 1.21 (6H, brs, 25-, 26-, and 27-methylene protons), 1.62 (2H, s, 24-methylene protons), 2.10–2.30 (4H, m, 18- and 23-methylene groups), 5.50–6.00 (4H, s+dd, s at 5.67 for 5-methylene protons, dd for 17-methylene protons), 7.80 (1H, s, 14-H), 7.99 (1H, s, 10-H), 8.23 (2H, s, 9-H and 11-H), 9.24 (1H, s, 7-H); $^{13}$C NMR(TFA): 8.63 (C19), 14.99 (C28), 24.66 (C27), 27.14 (C26), 31.07 (C24), 33.68 (C25), 34.29 (C18), 36.45 (C23), 54.34 (C5), 69.98 (C17), 79.50 (C20), 106.97 114.39, 118.55, 127.11, 132.41, 133.79, 134.55, 140.46, 141.11, 142.00, 145.79, 148.14, 150.62, 153.00 (C2, C3, C6–C16, C16a), 180.57, 193.10 (C21, C22); mass m/e (relative intensity 461 [(M+H)$^+$, 100%], 331 [(M—C$_6$H$_{13}$COO), 20%], 317 [(M—C$_6$H$_{13}$COO—CH$_3$+H), 10%], 303 [(M—C$_6$H$_{13}$COO—CO), 15%], 287 [(M—C$_6$H$_{13}$COO—CO$_2$), 8%], 273 (2%), 261 (2%).

Example 5-Camptothecin 20-O-nonanoate

To 40 ml methylene chloride in a 100 ml round—bottomed flask were added 5 ml nonanoyl chloride and 2 g starting camptothecin. The mixture was stirred under reflux for 48 h. After the solvent was evaporated by a rotary evaporator, the residue was chromatographically separated with methylene chloride—THF as eluent. The title compound, 169 mg, was obtained as a pale yellow powder, yield 6%, mp 180° C. $^1$H NMR in CDCl$_3$: 0.84 (3H, t, J=6.60 Hz, 30-methyl proyons), 1.02 (3H, t, J=7.69 Hz, 19-methyl protons), 1.20–1.80 (12H, m, 24–29 methylene protons), 2.10–2.38 (2H, m, 18-methylene protons), 2.40–2.60 (2H, m, 23-methylene protons), 5.33 (2H, s, 5-methylene protons), 5.40–5.80 (2H, dd, J=17.22, 17.22 Hz, 17-methylene protons), 7.26 (1H, s, 14-H), 7.71 (1H, t, J=8.06 Hz, 10-H), 7.88 (1H, t, J=8.43 Hz, 11-H), 7.99 (1H, d, J=7.33 Hz, 9-H), 8.26 (1H, d, J=8.79 Hz, 12-H), 8.44 (1H, s, 7-H); $^1$HNMR in TFA: 0.96 (3H, s, 30-methyl protons), 1.24 (3H, s, 19-methyl protons), 1.38 (10H, brs, 25–29-methylene protons), 1.87 (2H, m, 24-methylene protons), 2.40–2.90 (4H, m, 18- and 23-methylene protons), 5.74–6.07 (4H, s+dd, s at 5.91 for 5-methylene protons, dd with J=17.90, 18.21 Hz for 17-methylene protons), 8.05 (IH, s, 14-11), 8.24 (1H, t, 10-H), 8.48 (2H, m, 9-H and 11-H), 8.57(1H, d, 12-H), 9.48 (1H, s, 7-11); $^{13}$C NMR (TFA): 4.99 (C30), 11.45 (C19), 21.17 (C29), 23.53 (C28), 27.82 (C24, C26–27), 30.52 (C25), 30.63 (C18), 32.80 (C23), 103.28, 110.73, 114.91, 123.47, 128.79, 128.90, 130.14, 130.93, 136.84, 137.46, 138.33, 142.17, 144.47, 146.94 (C2, C3, C6–C16, C16a), 169.98, 176.92 (C21, C22); mass m/e (relative intensity): 489 [(M+H)$^+$, 100%], 33 1[(M—C$_8$H$_{17}$COO, 23%], 317 [(MC$_8$H$_{17}$COO—CH$_3$+11), 13%], 303 [(M—C$_8$H$_{17}$COO—CO), 17%], 287 [(M—C$_2$H$_{17}$COO—CO$_2$), 8%], 273 (3%), 216 (2%).

Example 6-Camptothecin 20-O-crotonate

Crotonic anhydride (40 ml) and pyridine (30 ml) were mixed in a 100 ml round-bottomed flask. To this solution, the starting camptothecin (8 g) was added. The mixture was stirred at 90±10° C. for 15 h. After cooling to room temperature, the crude product was precipitated in 1000 ml petroleum ether and collected by filtration. After column chromatography, the compound (3 g) was obtained, yield 31%, mp 218–220° C. (deformed at 155° C.). $^1$H NMR (CDCl$_3$): 1.00 (3H, t, J=7.51 Hz, 19-methyl protons), 1.94 (3H, dd, $J_{H25-H24}$=6.96 HZ, $J_{H25-H23}$=1.89 Hz, methyl protons), 2.15–2.35 (2H, m, 18-methylene protons), 5.28 (2H, s, 5-methylene protons), 5.38–5.74 (2H, dd, J=17.22, 17.22 Hz, 17-methylene protons), 5.99 (1H, d, J=13.92 Hz, 23-H), 7.05–7.14 (1H, dq, $J_{H24-H23}$=15.38 Hz, $J_{H24-H25}$=6.96 Hz, 24-H), 7.24 (1H, s, 14-H), 7.67 (IH, t, J=6.96 Hz, 10-H), 7.83 (1H, t, J=6.96 Hz, 11-H), 7.94 (1H, d, J=7.70 Hz, 9-H), 8.21 (IH, d, J=8.43 Hz, 12-H), 8.39 (1H, s, 7-H); mass m/e (relative intensity): 416 (M$^+$, 20%), 330 [(M—CH$_3$CH=CHCOOH), 100%], 315 [(M—CH$_3$CH=CHCOOH—CH$_3$), 40%], 302 [(M—CH$_3$CH=CHCOOH—CO), 73%], 287 [(M—CH$_3$CH=CHCOOH—CO$_2$+11), 30%], 274 (10%), 259 (9%), 246 (9%), 234 (3%), 218 (5%, 205 (4%), 191(3%); precise mass: found 416.137, C$_{24}$H$_{20}$N$_2$O$_5$ requires 416.137.

Example 7-Camptothecin 20-O-2',3'-epoxy-butyrate

To 50 ml benzene in a 100 ml round—bottomed flask were added 160 mg of the starting compound of Example 6 and 150 mg m-chloroperoxybenzoic acid (57–86%, Aldrich Chemical Co., Milwaukee, Wis.). The mixture was stirred at room temperature for a week. The solvent was removed by a rotary evaporator. The residue was chromatographically separated. The compound (120 mg) was obtained as white powder, yield 72%, mp: the compound deformed at 175° C. and decomposed at 210–213° C. $^1$H NMR (CDCl$_3$): 0.99 (3H, t, J=7.51 Hz, 19-methyl protons), 0.90–1.94 (3H, dd, $J_{H25-H24}$=6.96 Hz, $J_{H25-H23}$=1.84 Hz, 25-methyl protons), 2.07–2.33 (2H, m, 18-methylene protons), 5.30 (2H, s, 5-methylene protons), 5.38–5.72 (2H, dd, J=17.59, 17.95 Hz, 17-methylene protons), 5.95–6.02 (IH, dd, $J_{H23-H24}$=15.75 Hz, $J_{H23-H25}$=1.83 Hz, 23-H), 7.04–7.12 (1H, dq, $J_{H24-H25}$=6.59 Hz, $J_{H24-H23}$=15.38 Hz, 24-H), 7.22 (1H, s, 14-H), 7.75–8.01 (4H, m, 9–12 aromatic protons), 8.78 (1H, d, J=8.06 Hz, 7-H); mass m/e (relative intensity): 432 (M$^+$, 28%), 416 [(M—O), 12%], 346 [(M—C$_4$H$_6$O$_2$), 100%], 331 [(M—C$_4$H$_5$O$_3$), 53%], 318 [(M—C$_4$H$_6$O$_2$—CO), 75%], 303 [(M—C$_4$H$_5$O$_3$—CO, 54%], 287 [(M—C$_4$H$_5$O$_3$—CO$_2$), 27%], 275 (15%), 259 (7%), 246 (8%), 231 (5%), 218 (8%), 205 (10%, 191 (5%; precise mass: found 432.132, C$_{24}$H$_{20}$N$_2$O$_6$ requires 432.132.

Example 8–9-Nitrocamptothecin 20-O-acetate

Acetic anhydride (3 ml) and pyridine (2 ml) were mixed in a 50 ml round—bottomed flask in which 140 mg 9-nitrocamptothecin was placed. The mixture was stirred at room temperature for 24 h. The mixture was then separated by chromatotron. The title compound, 70 mg, was obtained as a yellow powder, yield 45%, mp 195° C. (deformed at 165° C.). $^1$H NMR (CDCl$_3$): 1.02 (3H, t, J=7.51 Hz, 19-methyl protons), 2.10–2.40 (5H, s+m, s at 2.26 for 23-methyl protons, m for 18-methylene protons), 5.40 (2H, s, 5-methylene protons), 5.41–5.75 (2H, dd, J=17.59, 17.95 Hz, 17-methylene protons), 7.23 (1H, s, 14-H), 7.96 (1H, t, J=6.96 Hz, 11-H), 8.53 (1H, d, J 10.99 Hz, 10-H), 8.58 (1H, d, J=9.98 Hz, 12-H), 9.31 (1H, s, 7-H); mass m/e (relative intensity): 435 (M$^+$, 25%), 375 [(M—CH$_3$COOH), 100%], 360 [(MCH$_3$COOH—CH$_3$), 40%], 347 [(M—CH$_3$COOH—CO), 87%], 332 [(M—CH$_3$COOH—CO—CH$_3$), 37%], 319 (13%), 302 (11%), 291 (10%), 286 (11%), 274 (10%), 258 (4%), 246 (5%), 216 (8%); precise mass: found 435.107, C$_{22}$H$_{17}$N$_3$O$_7$ requires 435.107.

Example 9–9-Nitrocamptothecin-20-O-propionate

Using 6 ml propionic anhydride, 5 ml pyridine, and 600 mg starting 9-nitrocamptothecin, the reaction was carried out in the same manner as in Example 8. After the reaction, the crude product was allowed to precipitate from 200 ml petroleum ether, collected by filtration, separated by column chromatography, and purified by reprecipitation from 200 ml petroleum ether. The pure compound (500 mg) was obtained as a yellow powder, yield 73%, mp 163° C. (deformed at 155° C.). $^1$H NMR(CDCl$_3$): 0.99 (3H, t, J 7.51 Hz, 19-methyl protons), 1.18 (3H, t, J=7.46 Hz, 24-methyl protons), 2.10–2.30 (2H, m, 18-methylene protons), 2.52–2.70 (2H, m, 23-methylene protons), 5.37 (2h, s, 5-methylene protons), 5.39–5.73 (2H, dd, J=17.58, 17.58 Hz, 17-methylene protons), 7.22 (1H, s, 14-H), 7.93 (1H, t, J=8.06 Hz, 11-H), 8.50 (1H, d, J=10.60 Hz, 10-H), 8.54 (1H, d, J=8.43 Hz, 12-H), 9.28 (1H, s, 7-H); mass m/e (relative intensity): 449 (M$^+$, 28%), 375 [(M—C$_2$H$_5$COOH), 100%], 360 [(M—C$_2$H$_5$COOH—CH$_3$), 35%], 347 [(M—C$_2$H$_5$COOH—CO), 82%], 332 [(M—C$_2$H$_5$COOH—CO—CH$_3$), 26%], 319 (9%), 302 (8%), 291(7%), 274 (7%), 258 (2%), 245 (2%), 216 (2%); precise mass: found 449.122, C$_{23}$H$_{19}$N$_3$O$_7$ requires 449. 122.butyrate.

Example 10-9-Nitrocamptothecin 20-O-butyrate

Using 2 ml butyric anhydride, 2 ml pyridine, and 60 mg starting 9-nitrocamptothecin, the procedure for preparation of the compound was the same as Example 8. The title compound (40 mg) was obtained as a yellow powder, yield 56%, mp 182° C. $^1$H NMR (CDCl$_3$): 0.98 (6H, m, 19- and 25-methyl groups), 1.65–1.70 (2H, m, 24-methylene protons), 2.10–2.40 (2H, m, 18-methylene protons), 2.41–2.60 (2H, m, 23-methylene protons), 5.36 (2H, s, 5-methylene protons), 5.38–5.72 (2H, dd, J=17.59, 17.96 Hz, 17-methylene protons), 7.22 (1H, s, 14-H), 7.92 (1H, t, J=7.52 Hz, 11-H), 8.49 (1H, d, J=10.80 Hz, 10-H), 8.53 (1H, d, J=9.53 Hz, 12-H), 9.27 (1H, s, 7-H); mass m/e (relative intensity): 463 (M+, 14%), 375 [(MC$_3$H$_7$COOH), 100%], 360 [(M—C$_3$H$_7$COOH—CH$_3$), 32%], 347 [(M—C$_3$H$_7$COOH—CO), 78%], 332 [(M—C$_3$H$_7$COOH—CO—CH$_3$), 25%], 319 (9%), 302 (8%), 291(7%), 274 (7%), 258 (2%), 245 (3%), 216 (5%); precise mass: found 463.137, C$_{24}$H$_{21}$LN$_3$O$_7$.

Example 11

Identical cultures of HL-60 cells received 0.2 μm of 20(S) CPT or 0.2 μM of a CPT ester (identified in FIG. 17) and cell cycle perturbations and apoptosis were detected by flow cytometry analysis of the relative DNA count using an Epics-Elite laser flow cytometry (Coulter) and analyzed with the Multicycle program (Phoenix Flow Systems). Histograms A,H,Q: untreated cells; B,I,P:+CPT; C,J,Q:+CPT-acetate; D,K,R:+SF6A; E,L,S:+SF6B; F,M,T:+SF6C; G,N, U:+SF6D. The cells were treated for 24 hr (A,B,C,D,E,F,G), 72 hr (H,I,J,K,L,M,N) and 120 hr (O,P,Q,R,S,T,U). See FIG. 17 for meaning of SF6 numbers. G$_1$=G0+G1 cells; G2=G2+M cells; AP=apoptotic cells. The number in parenthesises indicates percent of apoptotic cells in the cell culture. The results are shown in FIG. 18.

Example 12

Figure 17:
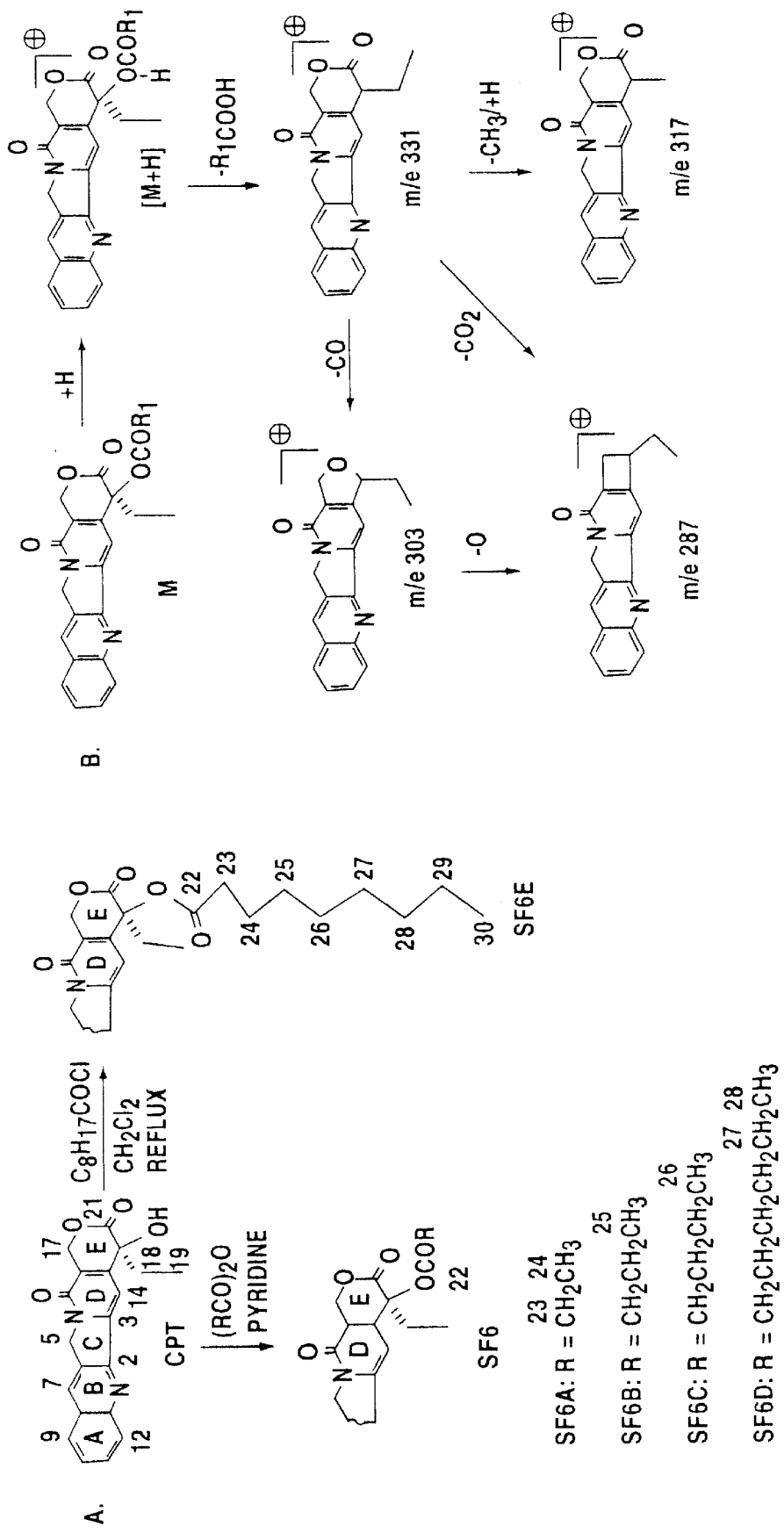
FIG. 17 sets forth the chemical structures of several CPT derivatives used in experiments.
Figure 18:
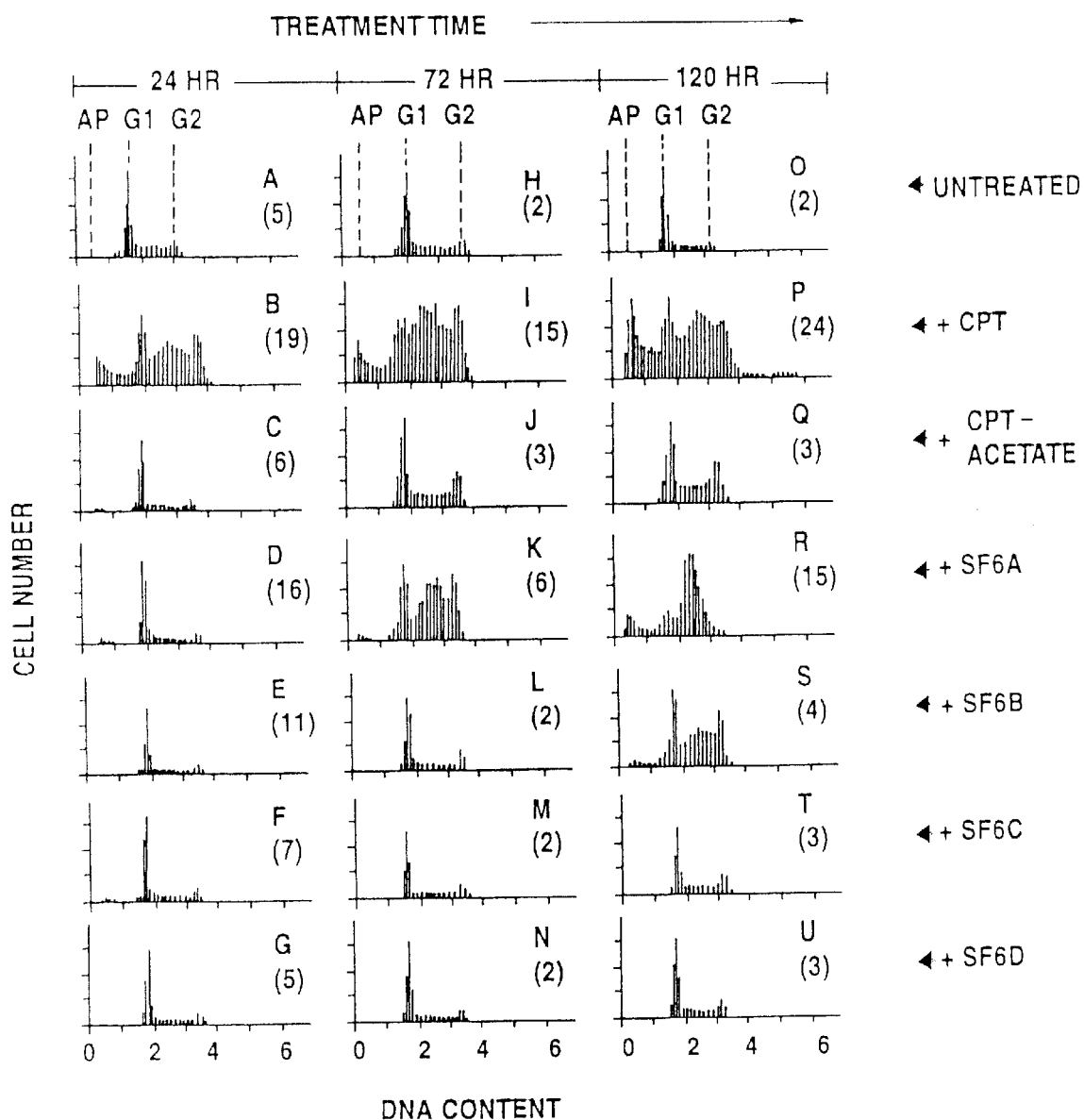
FIG. 18 shows the results of flow cytometry indicating treatment time, cell number, and DNA content for 20(S) CPT and CPT derivatives.
Figures 19, 19A, 19B:
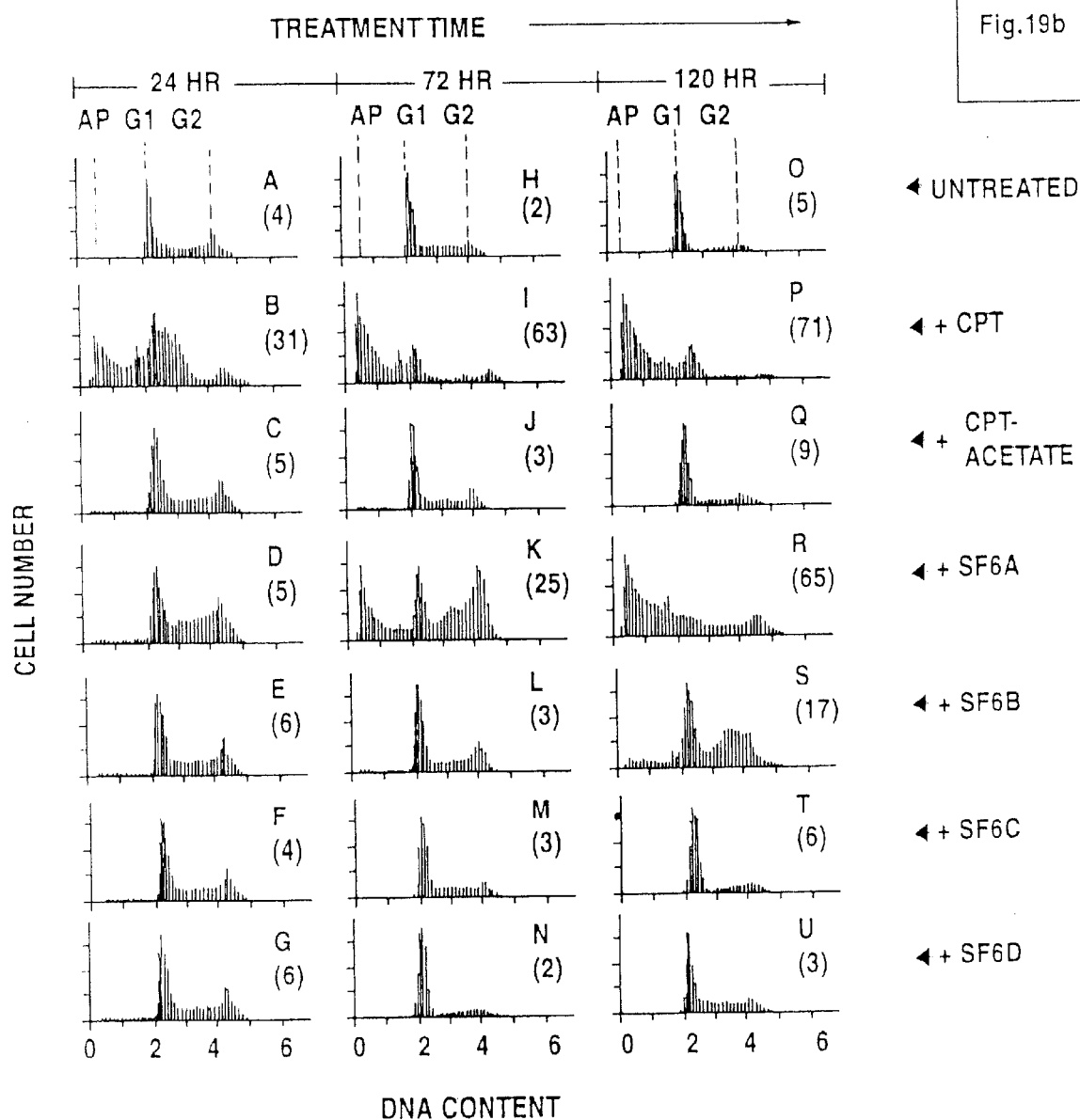
FIG. 19 also shows a flow cytometry analysis for 20(S) CPT and CPT derivatives reflecting treatment time, cell number, and DNA content.
Figure 19B:
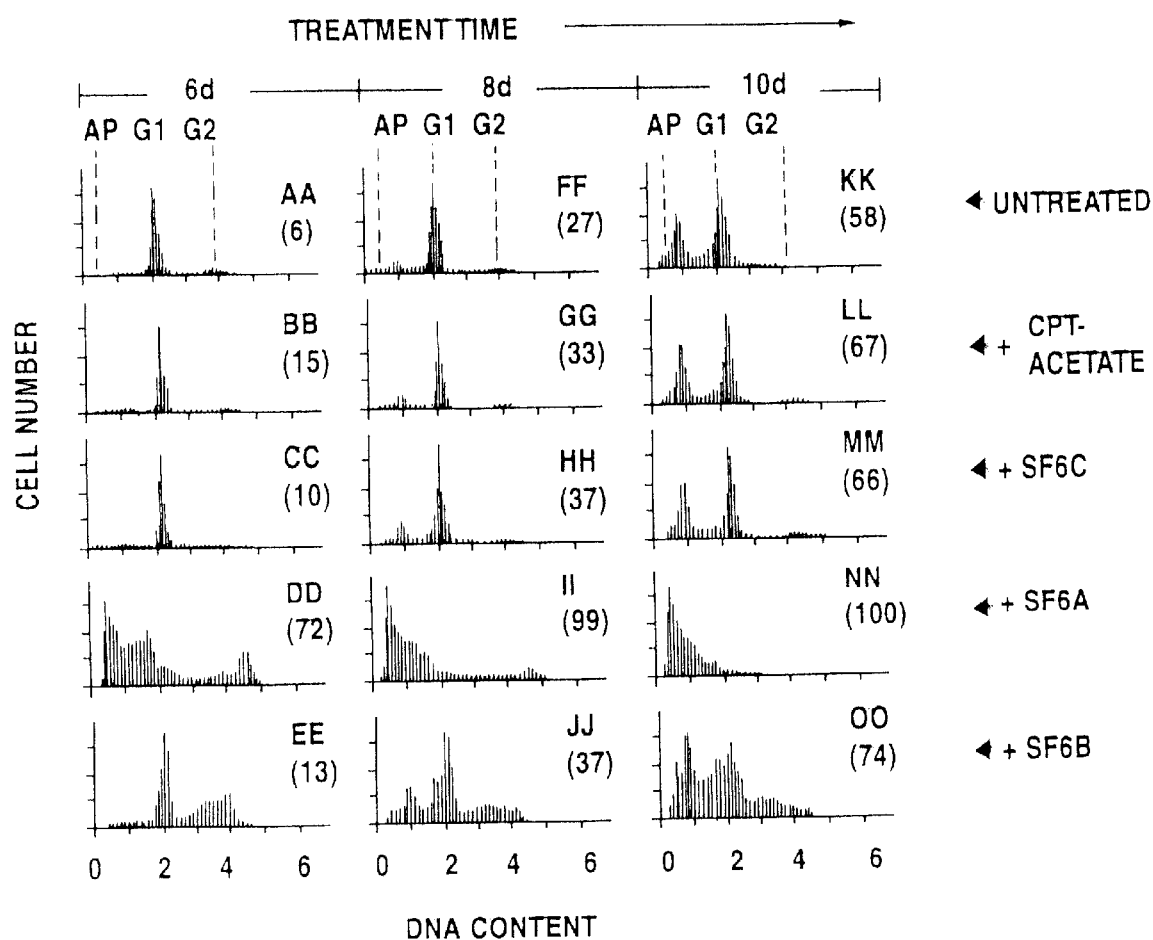

U-937 cells were treated with 0.2 μm of each compound identified in FIG. 17 (including 20(S) CPT), then analyzed by flow cytometry as reflected in FIG. 18. U-937 cells were untreated (AA,FF,KK) or treated with 0.21 μM of CPT-acetate (BB,GG,LL), SF6C (CC,HH,MM) SF6A (DD,II, NN) and SF6B (EE,JJ,OO) for 6 days (BB,CC,DD,EE), 8 days (FF,GG,HH,II,JJ) and 10 days (KK,LL,MM,NN,OO), then subjected to flow cytometry analysis. The results are set forth in FIG. 19.

Example 13

Figure 20:
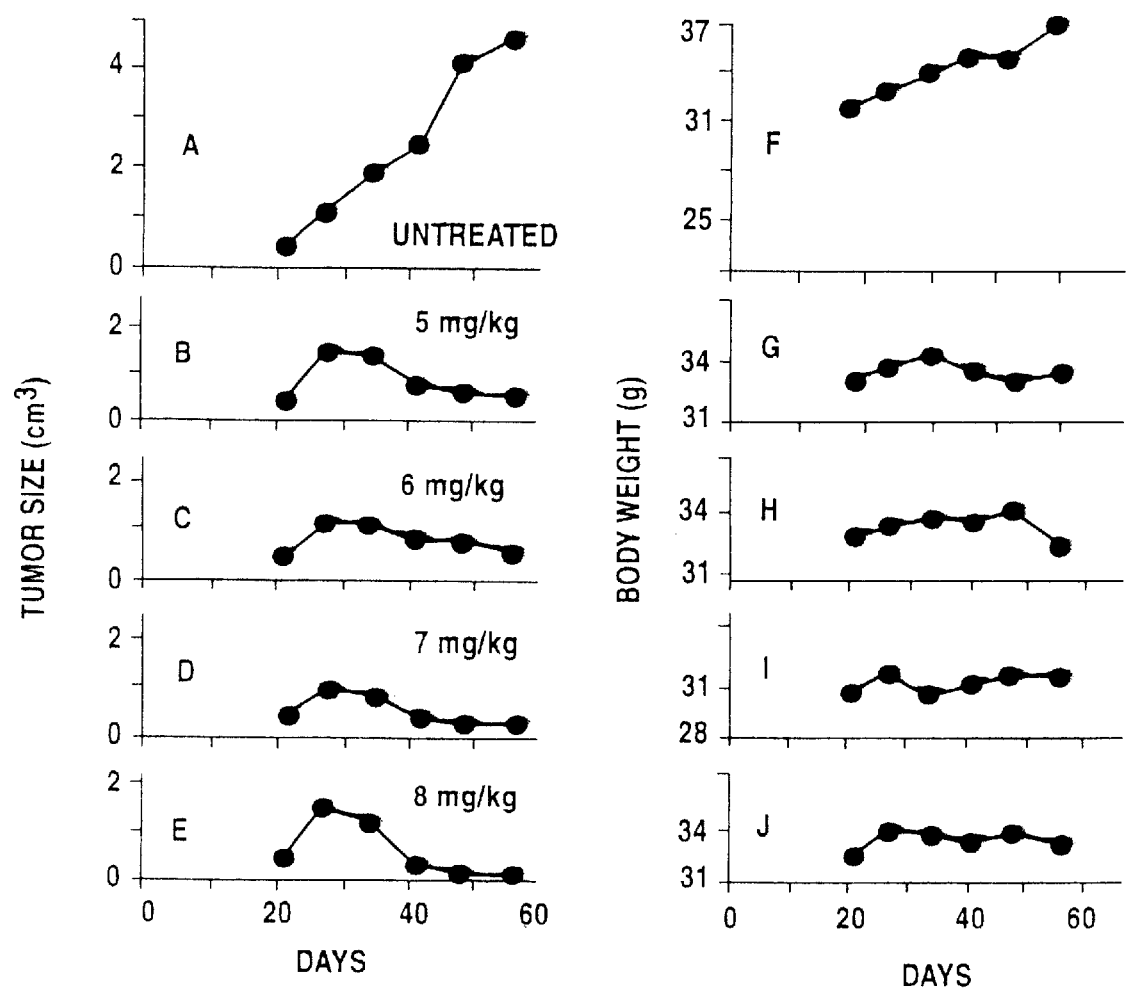
FIG. 20 is a set of graphs showing the results obtained for breast carcinoma in nude mice treated with CPT derivatives by intrastomach means.

Human breast tumors were grown as xenografts in nude mice and were allowed to reach measurable size before treatment with SF6A was initiated. Tumor bearing but untreated mice served as a control (A,F). SF6A was administered intragastrically using doses of 5 mg/kg (B,G), 6 mg/kg (C,H), 7 mg/kg (D,I) and 8 mg/kg (E,J). Maintenance, xenografting, drug treatment and tumor measurements were performed according to procedures described above. Tumor size (in cm$^3$) and body weight (in g) were measured as functions of the treatment period (in days). Tumor size: panels A,B,C,D,E,; and Body weight: panels F,G,H,I,J are shown in FIG. 20.

Example 14

Growth inhibition of U-937 cells treated with various CPT esters

Each identified compound was added to reach a culture of U-937 cell having a final concentration of 0.2 μM. The treatment time was for 120 hr. Growth inhibition in each of the treated cultures was then estimated as a percent of the exponential growth of the cells that was considered 100%. Each estimate was the mean value of four estimates. The results are set forth on the Table below.

| Treatment | Growth % |
| --- | --- |
| Untreated cells | 100 ± 2 |
| +CPT | 0.0 |
| +CPT-acetate | 92 ± 4 |
| +SF6A | 31 ± 2 |
| +SF6B | 44 ± 2 |
| +SF6C | 96 ± 5 |
| +SF6D | 92 ± 5 |
| +SF6E | 94 ± 4 |

Example 15

Determination of SF6A (Prodrug 2) and CPT in liver homogenate

Mouse liver was homogenized in 4 volumes of ice-cold 0.15 M KCl with the aid of a Dounce homogenizer, then centrifuged at 15000 G for 10 min to remove particulate material. The supernatant, designated as liver homogenate, was transferred into a capped polypropylene tube, mixed with 2 μg SF6A/ml and incubated in a 37° C. water-bath. At the desired times, samples were removed and mixed with 4 volumes of ice-cold ethanol to precipitate proteins. The samples were stored at −20° C. until all were collected. Following centrifugation at 15000 G for 10 min, the clarified supernatants were subjected to analysis for determination of SF6A and CPT lactones by high pressure liquid chromatography (HPLC). The compounds were detected by fluorescence spectroscopy setting the excitation and emission wavelengths at 347 nm and 418 nm, respectively. CPT and SF6A have characteristic retention times of 3.5 min and 13.5 min, respectively. The results are shown in the Table below.

| Incubation | Amount determined ($\mu$g/ml) | |
|---|---|---|
| time | SF6A | CPT |
| 0 min | 1.95 | 0.00 |
| 10 min | 2.06 | 0.00 |
| 60 min | 2.05 | 0.00 |
| 6 hr | 2.05 | 0.00 |
| 24 hr | 0.96 | 0.47 |
| 48 hr | 0.90 | 0.30 |

Example 16

Stability of lactone forms of CPT and SF6A in the human plasma

CPT or SF6A lactone was added to human plasma (1 $\mu$g/ml) and an incubation and lactone determination were made as described in Example 15. The lactone amount at each time-point was detected after removing the carboxylate form, and subsequently was calculated as percent of the initial lactone amount added. The results shown in this Table below were derived from one of the three independent experiments performed using different incubation times. The pattern of quantitation of the lactones was similar in all three experiments.

| Incubation | Percent in plasma | |
|---|---|---|
| time (hr) | CPT lactone | SF6A lactone |
| 0.0 | 100.0 | 100.0 |
| 0.5 | 40.0 | NT |
| 1.0 | 12.0 | 86.0 |
| 2.0 | 0.5 | 77.0 |
| 4.0 | 0.0 | 68.0 |
| 6.0 | 0.0 | 56.0 |
| 27.0 | 0.0 | 9.0 |

Example 17

Swiss nude mice of the NIH high fertility strain were bred and maintained pathogen-free in a laboratory. (Giovanella, B. C. and Stehlin, J. S. "Heterotransplantation of human malignant tumors in 'nude' thymusless mice. I. Breeding and maintenance of 'nude' mice." J. Natl. Cancer Inst. 51: 615–619; 1973.)

Human malignant carcinomas of the colon, breast, lung, ovary, stomach, pancreas, bladder, prostate, osteosarcoma and malignant melanomas were heterotransplanted directly from a patient into the nude mice and passaged serially. In particular, the tumors CLO, MUR, CAS, SW 48, SQU and BRO as described in Giovanella, B. C., Stehlin, J. S., Shepard, R. C. and Williams, L. J. "Correlation between response to chemotherapy of human tumors in patients and in nude mice." Cancer 52: 1146–1152; 1983, tumor SCH as described in Heim, S., Mandahl, N., Arheden, K., Giovanella, B.C., Yim, S. O., Stehlin, J. S., Jr. and Mitehman, F. "Multiple karyotypic abnormailites including structural rearrangements of 11P in cell lines from malignant melanomas." Cancer Genet. Cytogent, 35:5–20; 1988, and Verschraegen, C., Giovanella, B. C., Mendoza, J. T., Kozielski, A. J. and Stehlin, J. S., Jr. "Specific organ metastases of human melanoma cells injected into the arterial circulation of nude mice." Anticancer Res., In Press, and tumor PC-3 as described in Invest. Urol. 17, 16–23, 1979, were used. Tumors DOY and HAR (undifferentiated non-oat cell carcinomas of the lung), DIL (a poorly differentiated squamous cell carcinoma of the lung), SPA (a moderately differentiated adenocarcinoma of the lung), LAN (an undifferentiated carcinoma of the ovary), and BRE (a moderately differentiated adenocarcinoma of the stomach) where heterotransplanted. For the experiments, the tumor tissue was finely minced in complete MEM medium and 0.5 ml of a 10% v/v suspension was inoculated subcutaneously on the upper back of groups of 10–30 mice. When the tumors became palpable and measurable in all the animals, they were divided into groups of 4–8 and treated with the desired dose of the drug in experiment or with the vehicle only for the controls.

A typical sample preparation for IM-injection or oral administration using Intralipid 20 or cottonseed oil for example includes the dispersion of the test compound by sonication (3 pulses for 30 seconds each) in Intralipid 20 or cottonseed oil at the standard concentration of 1 mg/ml injections were performed through a 27-gauge needle into the deep muscles of the prosterior legs of the mice twice a week. The animals received up to 70 such injections consecutively without suffering ill effects except for some local fibrosis. Intravenous injections, using intralipid 20 as the suspending agent, were performed through a 30-gauge needle in one of the trial veins. No pulmonary embolism was observed after over 200 injections.

Oral administration was achieved by mixing the required amounts of drugs Intralipid 20 or cottonseed oil with a previously autoclaved dietary supplement composed of whole wheat bread saturated with whole milk. The supplement containing the drug was then thoroughly mixed to form a paste. Mice were fed 1 g of dietary supplement containing the required dose of the drugs once a day and then 5 g of autoclaved mouse feed. (At this regime, the animals initially lose about 4 g out of 30 g of body weight, regain 2 g within a few days, and stabilize at this level). This regime can be carried on indefinitely. Actually, the mice fed in this manner (a slightly lower maximum caloric intake) were healthier and longer-lived then mice fed ad lib (Giovanella, B. C., Shepard, R. C., Stehlin, J. S., Venditti, J. M. and Abbott, B. J. "Calorie restriction: Effect on growth of human tumors heterotrarsplanted in nude mice." J. Natl. Cancer Inst. 68: 249–257; 1982). Oral administration was accomplished by injecting the mixture of compound with cottonseed oil directly into the stomach (IS). Table 3 below provides some of the results obtained by the treatment with CPT and derivatives thereof, and the description and Figures thereafter provide additional results.

TABLE 3

| Tumor | Treatment Of Prodrug 2 | # of Animals | Results | # of Treatments | Observations |
|---|---|---|---|---|---|
| BreastCa CLO | IM, 2x/wk 4 mg/kg | 5 | 3/5 CR 2/5 PR | 13 | Day 63, 5/5 Alive, 4/5 Controls Alive |
| BreastCa CLO | IM, 2x/wk 5 mg/kg | 5 | 3/5 PR 2/5 PR | 9 | Day 56, 4/5 Alive, 1 inj. Death, 5/5 Controls Alive |
|  | IM, 2x/wk 6 mg(kg | 5 | 2/5 PR 3/5 PR | 9 | 4/5 Alive, 1 inj. Death |
|  | IM, 2x/wk 7 mg/kg | 5 | 4/5 CR 1/5 PR | 9 | 5/5 Alive |
|  | IM, 2x/wk 8 mg/kg | 5 | 5/5 CR | 9 | 5/5 Alive |
| CLO | IM, 2x/wk 12 mg/kg | 3 | 3/3 CR | 26 | Day 110, 3/3 Alive, 0/4 Controls Alive |
|  | IM, 2x/wk 16 mg/kg | 4 | 4/4 CR | 26 | 3/4 Alive |
|  | IM, 2x/wk 20 mg,kg | 2 | 2/2 CR | 26 | 2/2 Alive |
| Colon Ca SW48 | IS. 5 +/2– 20 mg/kg | 6 | 6/6 PR | 28 | Day 62, 6/6 Alive, 2/6 Controls Alive |
| SQU | IS. 5 +/2– 30 mg/kg | 6 | 3/6 CR 2/6 PR 1/6 NR | 68 | Day 111, 5/6 Alive, 1/6 Controls Alive |
|  | IS. 5 +/2– 50 mg/kg | 6 | 5/6 CR 1 PR | 68 | 4/6 Alive |
|  | IS. 5+/2– 70 mg/kg | 6 | 4/6 CR 2/6 PR | 68 | 5/6 Alive |
| LungCA SPA | IS. 5 +/2– 100 mg/kg | 4 | 314 CR 1/4 PR | 65 | Day 41, 4/4 Alive, 1/4 Controls Alive, Day 90 4/4 Alive, 1/4 Controls Alive, Day 107, 1/4 Alive, 1/4 Controls Alive |
| Colon CA HT29 | IS. 5 +/2– 100 mg/kg | 5 | 1/5 CR 1/5 PR 3/5 NR | 48 (injection stopped, day 82) | Day 74, 4/5 Alive, 1/5 Controls Alive, Day 116 1/5 Alive, 0/5 Controls |
|  | IS. 5 +/2– 200 mg/kg | 5 | 3/5 CR 1/5 PR 1/5 NR | 48 (injection stopped, day 82) | Day 74, 4/5 Alive Day 116 2/5 Alive |
|  | IS. 5 +/2– 300 mg/kg | 5 | 4/5 CR 1/5 PR | 51 (injection stopped, day 87) | Day 74, 4/5 Alive Day 116 4/5 Alive |

CR — Complete remission defined as total disappearance of the initial tumor, maintained for a least 30 days at teh making of this table.
NR — No response
PR — Partial response
W — Week
D — Daily
Unless otherwise noted, all i.m. and i.v. doses are administered 2x week, all oral doses daily.

Figure 9:
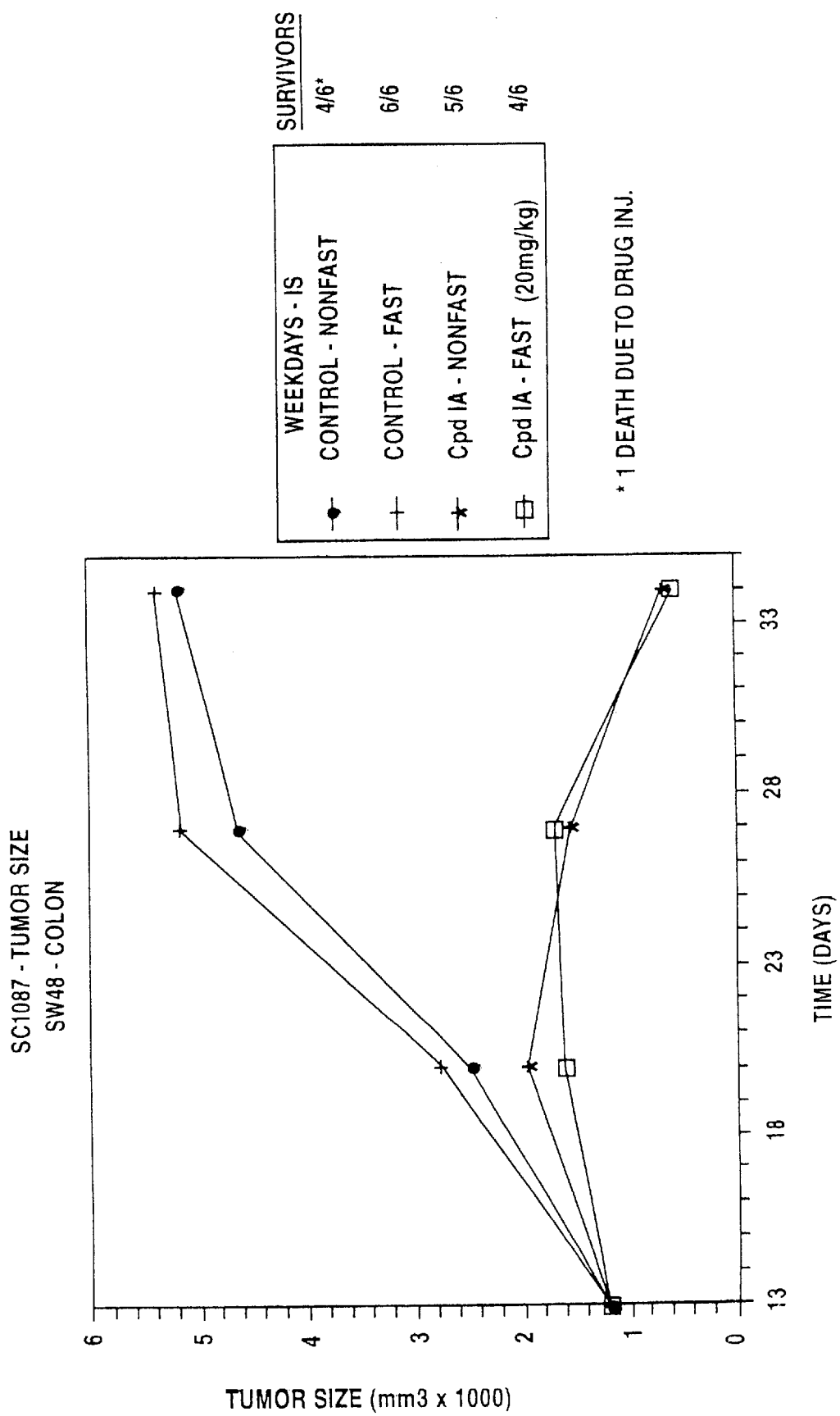
FIG. 9 is a graph which shows the results obtained for SW48 colon carcinoma in nude mice treated 5 times a week with a CPT derivative of the present invention at the dosage of 20 mg/kg by intrastomach means.

FIG. 9 shows the effectiveness of a compound of formula (I) wherein $R_2$ is $NO_2$ and $R_1$ is a ethyl group (hereinafter "Compound IA"), against colon cancer when administered by interstomach means. One group of six nude mice where treated interstomach with 10 or 20 mg/kg body weight Compound IA in cottonseed oil per day for five consecutive days with two day intervals of no treatment (i.e., five days of treatment then two days no treatment, and five day treatment and so on). Another group of six nude mice were treated with 10 or 20 mg/kg body weight Compound IA in the same manner. There were also two control groups of six nude mice each. The designation of "fast" means no food was fed to the mice for at least 12 hours before treatment and the designation of "non-fast" means fed normally. Thus, in this experiment, there were 4 groups of mice with 6 mice in each group. The treatment was ended after 34 days and FIG. 9 shows the results from day 13–34 wherein those mice receiving Compound IA saw a decline in the tumor size while the tumor size in the two control groups continued to increase in size.

Figure 10:
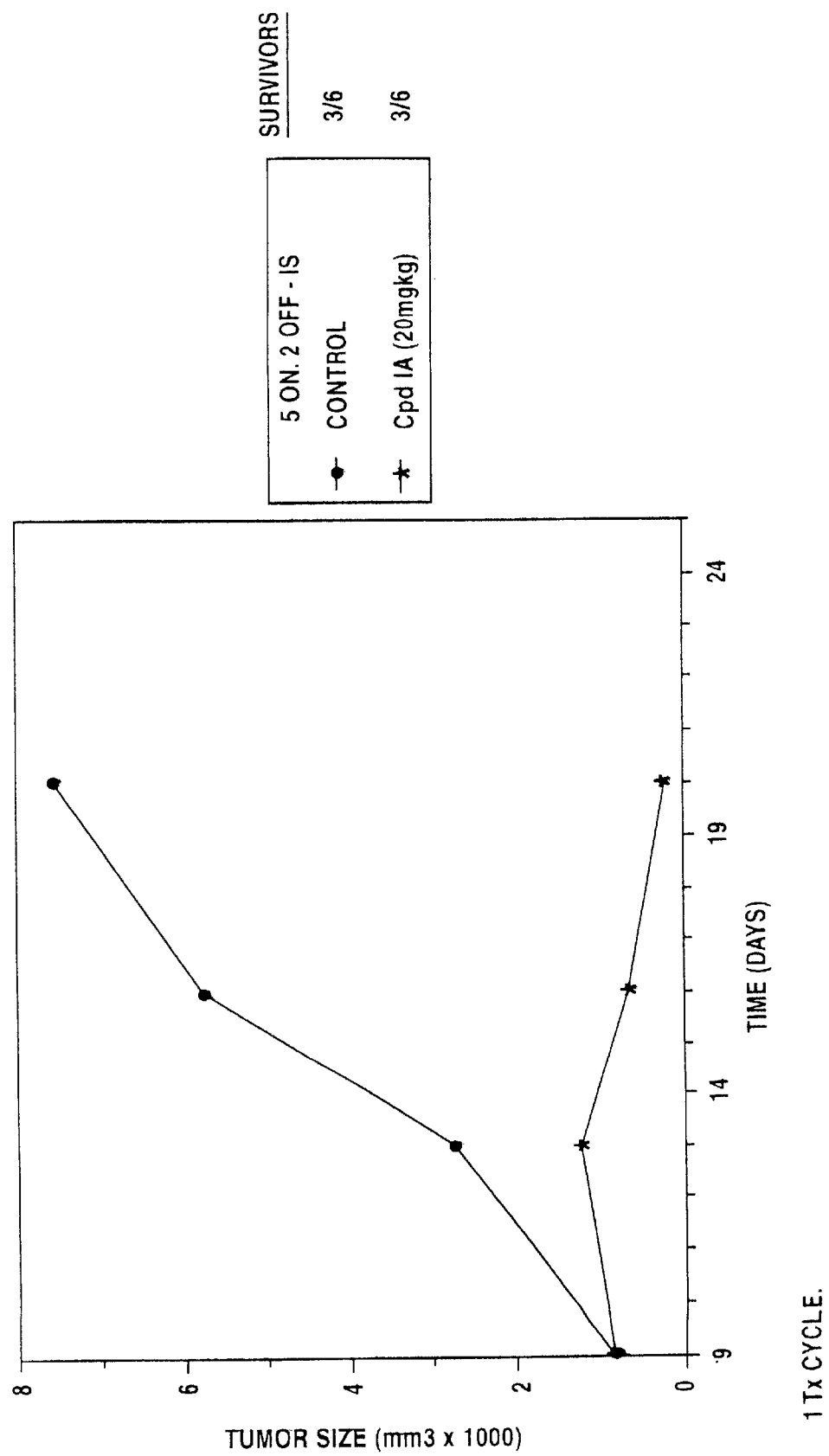
FIG. 10 is a graph which shows the results obtained for BRO melonoma in nude mice treated with a CPT derivative of the present invention at the dosage of 20 mg/kg by intrastomach means.

FIG. 10 shows the effectiveness of Compound IA on melanoma where the treatment regimen and number of mice were the same as in FIG. 9 except there was only one control group and one Compound IA tested group. The treatment was ended after 20 days and as can be seen in FIG. 10, the tumor size in the mice receiving Compound IA decreased in size while the tumor size in the control group increase dramatically.

Figure 11:
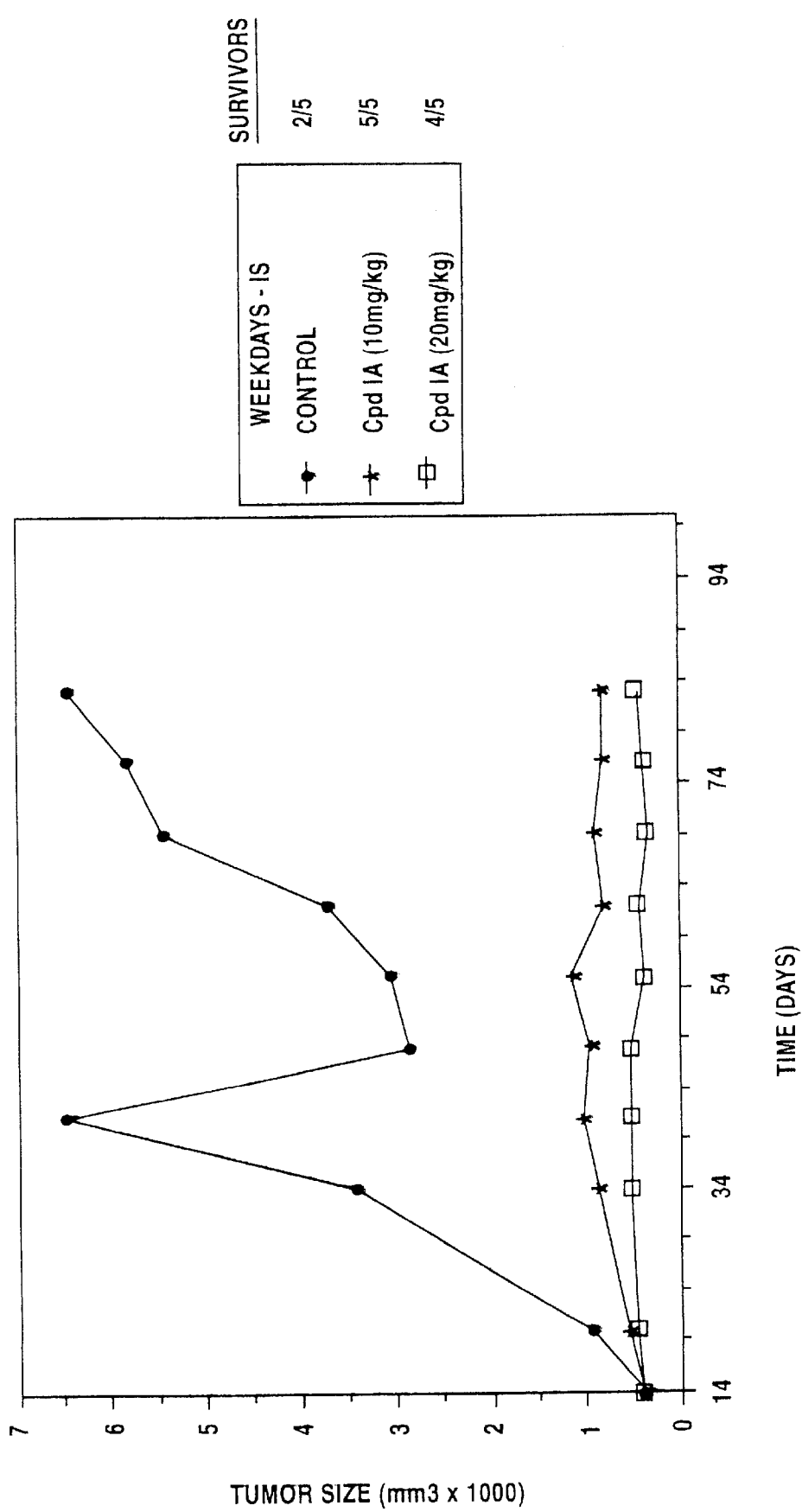
FIG. 11 is a graph which shows the results obtained for BRE stomach carcinoma in nude mice treated with a CPT derivative of the present invention at a dosage of 10 and 20 mg/kg respectively by intrastomach means.

FIG. 11 shows the effectiveness of Compound IA on stomach cancer. The dosage regimen and manner of administration are the same as in FIG. 9 except there were 5 mice per group and only one control group. Again, the Compound IA showed a prevention of the growth in the tumor size over a number of days until the experiment was terminated on day 34. The control group showed a dramatic increase in tumor size and only 2 of the 5 mice survived the 84 day test.

Figure 12:
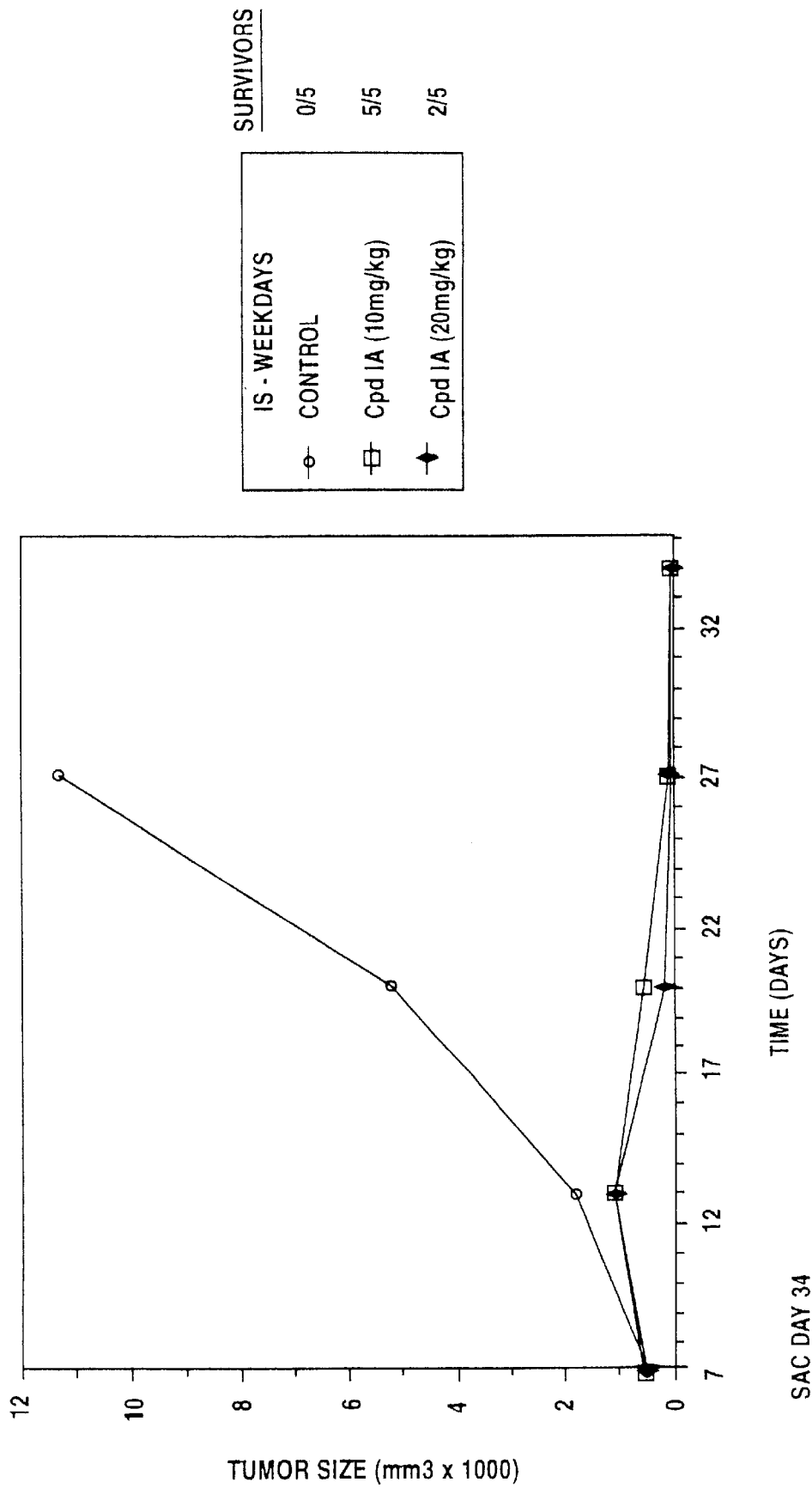
FIG. 12 is a graph which shows the results obtained for DOY lung carcinoma in nude mice reated with CPT derivative of the present invention at a dosage of 10 and 20 mg/kg respectively by intrastomach means.

FIG. 12 shows the effectiveness of Compound IA on lung cancer where the same dosage and administration regimen were used as in FIG. 9 except there were 5 mice per group and only one control group. As can be seen from FIG. 12, the tumor size showed a dramatic reduction over the length of the experiment which ended on day 34. None of the mice in the control group survived the experiment and in fact all mice were dead by day 27.

Figure 13:
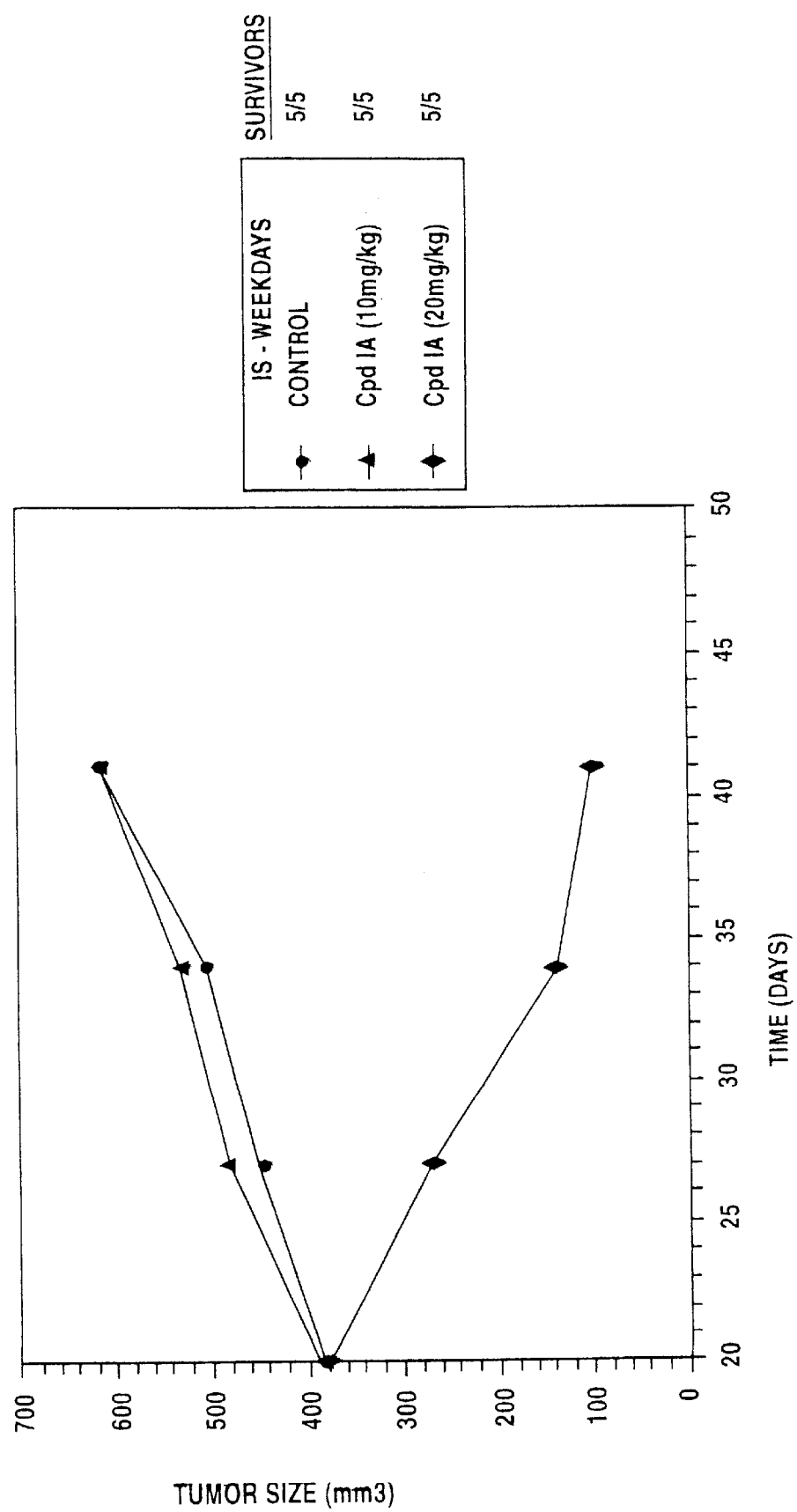
FIG. 13 is a graph which shows the results obtained for 2774 ovarian carcinoma in nude mice treated with a CPT derivative of the present invention at a dosage of 10 and 20 mg/kg respectively by intrastomach means.

FIG. 13 shows the effectiveness of Compound IA at high dosages against ovarian cancer. Unlike some other cancers, ovarian cancer was more resistant and thus high concentrations of Compound IA were more effective. The route of administration and the dosage regimen were the same as in FIG. 9 except there were only 5 mice in each group and only one control group was used. The experiment ended after day 41 and all mice survived the experiment in each group. The Compound IA administered in higher dosage amounts was quite effective in reducing the tumor size while the control group and the group receiving the lesser dosage amount of Compound IA showed a steady increase in tumor size throughout the experiment.

Figure 14:
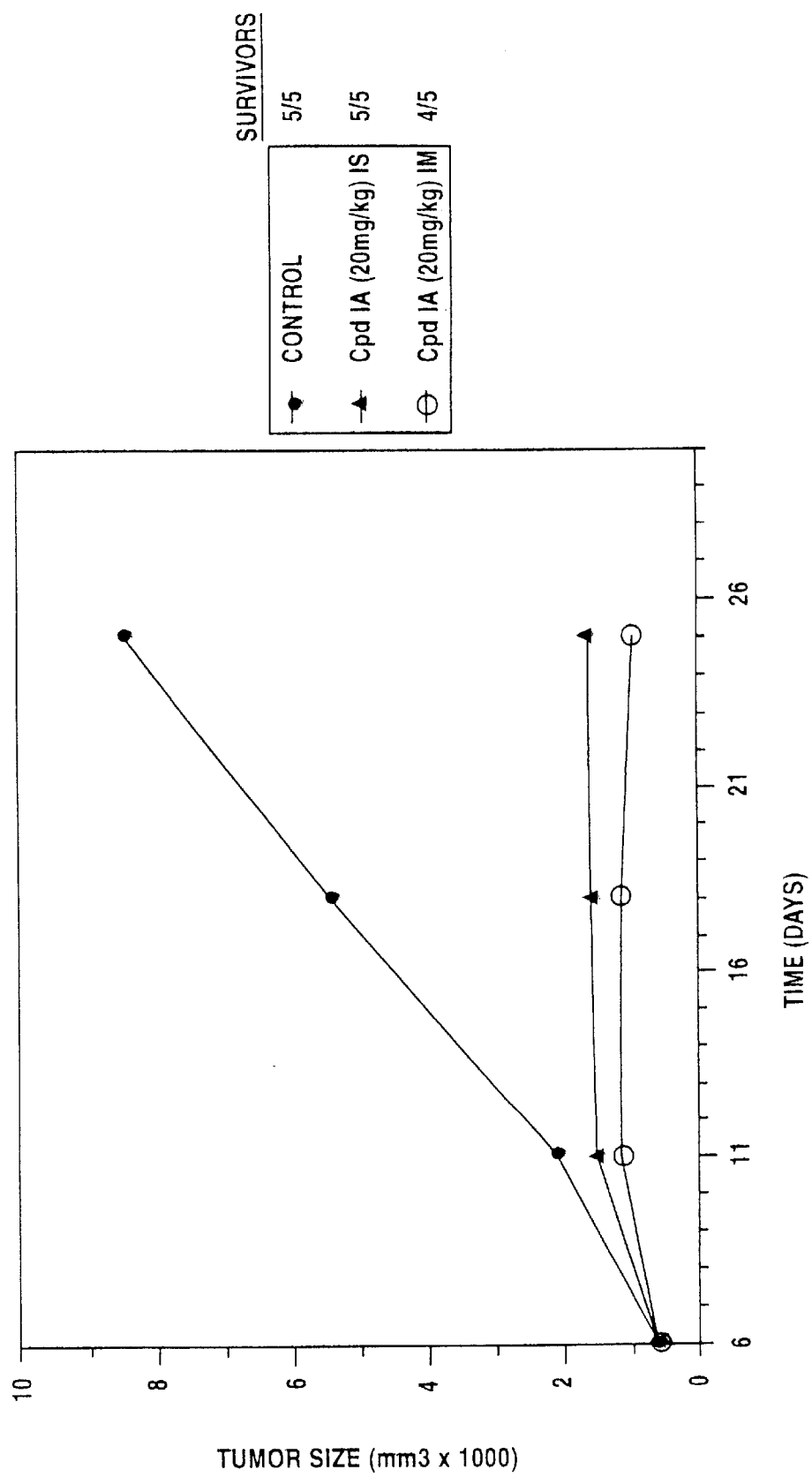
FIG. 14 is a graph which shows the results obtained for McC colon carcinoma in nude mice treated with a CPT derivative of the present invention at a dosage of 20 mg/kg by intrastomach or intramuscular means.

FIG. 14 shows the effectiveness of Compound IA against human colon cancer. One group of 5 mice received Compound IA by intrastomach means as in FIG. 9. The other group of 5 mice received the Compound IA in the same dosage amount by intramuscular means twice a week in the manner described above. As shown in FIG. 14, the tumor size in the groups of mice receiving the Compound IA increased slightly but then stabilized where there was no increase in the tumor size from day 11to the end of the experiment which was on day 25. The control, on the other hand, showed a steady increase in tumor size throughout the experiment from day 6 to day 25.

Figure 15:
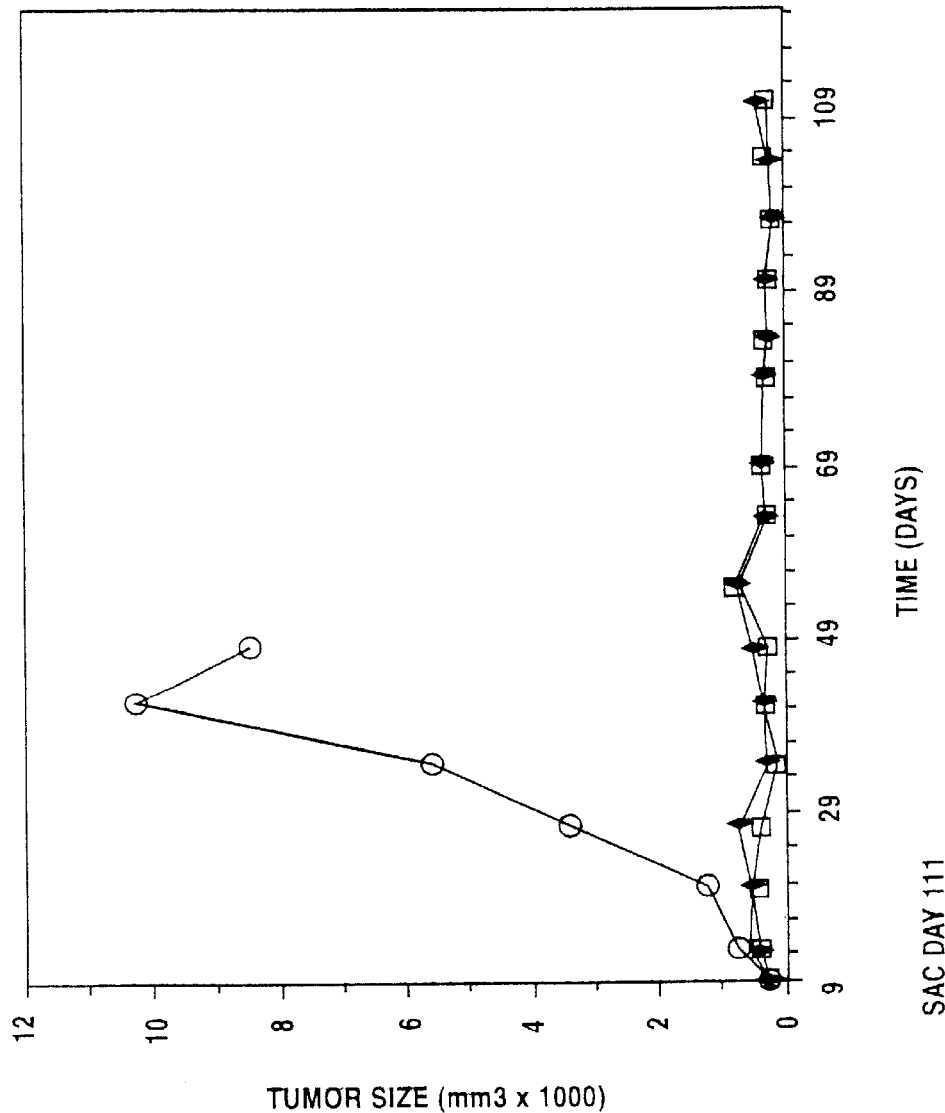
FIG. 15 is a graph which shows the results obtained for SQU colon carcinoma in nude mice treated with a CPT derivative of the present invention at a dosage of 10 mg/kg by intrastomach or intramuscular means.

FIG. 15 shows the effectiveness of Compound IA against another form of human colon cancer where there was one control group and one group of 6 mice that received Compound IA intramuscularly and one group of 6 mice that received the Compound IA by intrastomach means in the same manner as in FIG. 14. As shown in FIG. 15, the tumor size of the mice in the groups receiving Compound IA was essentially stabilized throughout the experiment which ended on day 111 while the tumor size for the control group showed a large increase in size until the mice in the control group all died which was on day 53.

Figure 16:
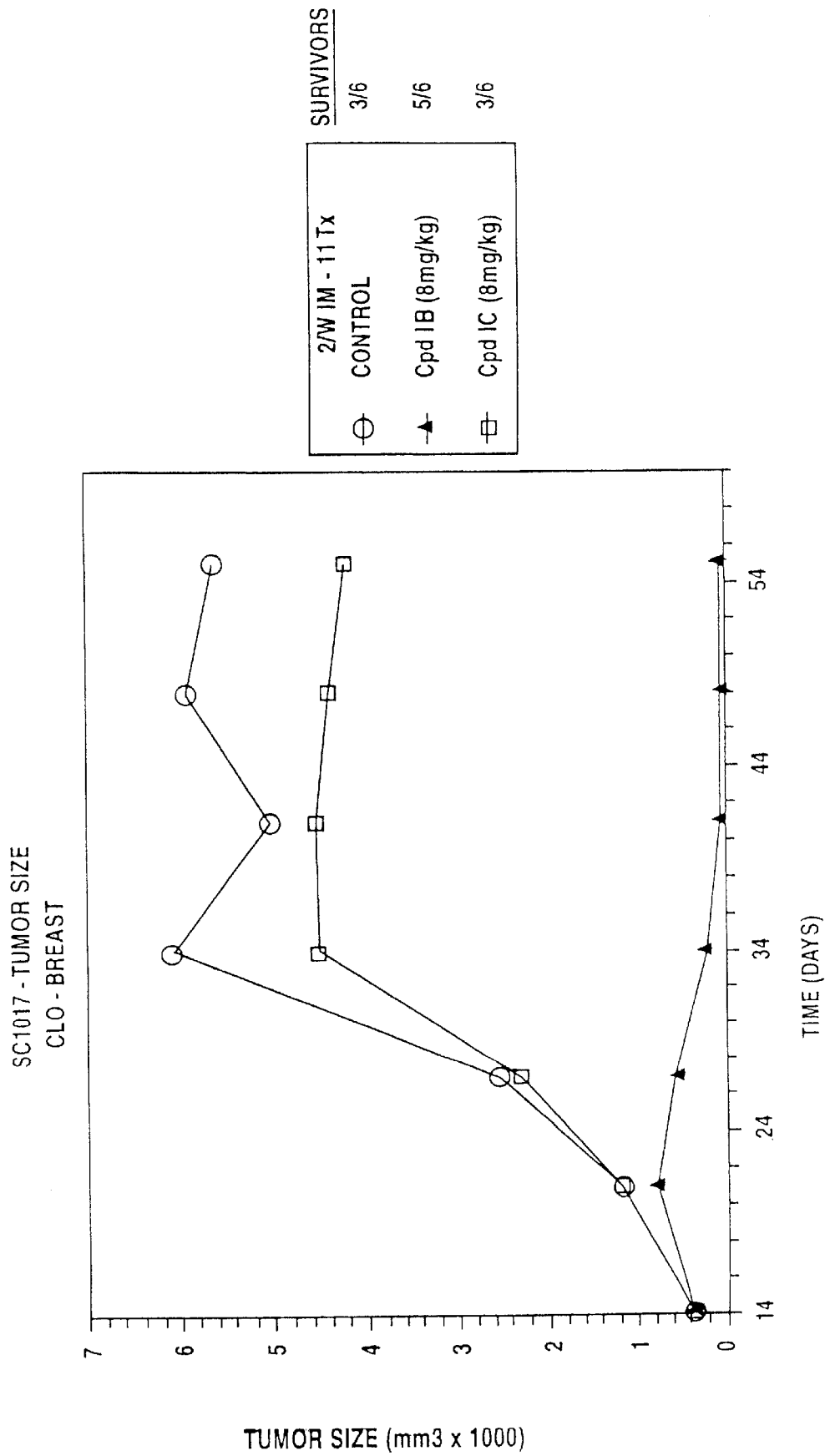
FIG. 16 is a graph which shows the results obtained for CLO breast carcinoma in nude mice treated with a CPT derivative of the present invention at a dosage of 8 mg/kg by intramuscular means.

FIG. 16 shows the effectiveness of Compound IB, which is a compound of formula (I) where $R_2$ is hydrogen and $R_1$ is a $C_3$ alkenyl group. FIG. 16 also shows the effectiveness of Compound IB which is a group of formula (I) where $R_2$ is hydrogen $R_2$ is a $C_3$ epoxy ring. In this experiment, a group of six mice received Compound IB in an amount of 8 mg/kg body weight twice a week and another group of six mice received Compound IC, which is a compound of formula (I), where $R_2$ is hydrogen and $R_1$ is a $C_3$ epoxy ring, in the same amount twice a week. In each case, the mice received the drug by intramuscular means in the manner described above. The experiment was ended after day 55. FIG. 16 shows the effectiveness of Compound IB in actually reducing the tumor size of the breast cancer, while Compound IC showed the ability to stabilize the tumor size after a certain amount of time and showed a lower tumor size than the control.

It is clear from these studies, that CPT derivatives have been demostrated to possess an astonishing level of anitcancer activity. This applies both to the spectrum of tumors covered and to the quality of the responses. The method of the present invention has been able to block growth completely and to totally regress human xenografts of carcinomas (e.g., lung, breast, colon, stomach, pancreas, bladder, prostate, osteosarcoma and ovaries) and malignant melanomas. This has been accomplished without any observable toxicity. Many of the mammals which have been treated continuously for six months have shown no ill effects nor regrowth of the tumor they once carried.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for transdermal administration comprising a patch containing a suspension or solution of an effective amount of a compound of formula (I):

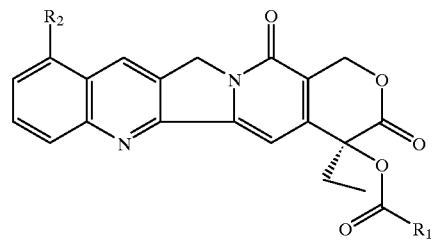

wherein $R_1$ is a $C_2$–$C_4$ alkyl group, a $C_6$–$C_{15}$ alkyl group, a $C_3$–$C_8$ cycloalkyl group, a $C_2$–$C_{15}$ alkenyl group or a $C_2$–$C_{15}$ epoxy group when $R_2$ is H; and $R_1$ is a $C_1$–$C_{15}$ alkyl group, a $C_3$–$C_8$ cycloalkyl group, a $C_2$–$C_{15}$ alkenyl group or a $C_2$–$C_{15}$ epoxy group when $R_2$ is $NO_2$.

2. The device of claim 1, wherein $R_1$ is a linear $C_2$–$C_4$ alkyl group or $C_6$–$C_{15}$ alkyl group when $R_2$ is H and $R_1$ is a linear $C_1$–$C_{15}$ alkyl group when $R_2$ is $NO_2$.

3. The device of claim 1, wherein $R_1$ is a linear $C_2$–$C_{15}$ alkenyl group.

4. The device of claim 1, wherein $R_1$ is a $C_2$–$C_{15}$ epoxy group.

5. A compound of claim 2, wherein $R_2$ is H.

6. The device of claim 2, wherein $R_2$ is $NO_2$.

7. The device of claim 3, wherein $R_2$ is H.

8. The device of claim 3, wherein $R_2$ is $NO_2$.

9. The device of claim 4, wherein $R_2$ is H.

10. The device of claim 4, wherein $R_2$ is $NO_2$.

11. The device of claim 2, wherein $R_1$ is a linear ethyl, propyl, butyl, hexyl or octyl group, and $R_2$ is H.

12. The device of claim 11, wherein $R_1$ is ethyl.

13. The device of claim 2, wherein $R_1$ is a linear methyl, ethyl or propyl group and $R_2$ is $NO_2$.

14. The device of claim 13, wherein $R_1$ is ethyl.

15. The device of claim 1, wherein $R_1$ is a $C_3$–$C_8$ cycloalkyl group.

16. The device of claim 15, wherein $R_2$ is H.

17. The device of claim 15, wherein $R_2$ is $NO_2$.

18. The device of claim 1, wherein $R_2$ is H, and $R_1$ is

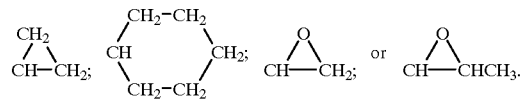

19. The device of claim 1, wherein $R_2$ is $NO_2$, and $R_1$ is

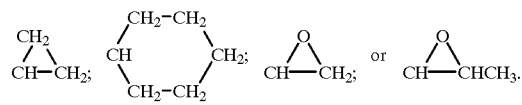

20. A method for treating a malignant tumor in a patient comprising administering a composition comprising an effective amount of the compound of claim 1, wherein said malignant tumor is responsive to said composition, wherein said compound is administered transdermally.

21. The method of claim 20, wherein $R_1$ is a linear $C_2$–$C_4$ alkyl group or a $C_6$–$C_{15}$ alkyl group where $R_2$ is H and $R_1$ is a linear $C_1$–$C_{15}$ alkyl group when $R_2$ is $NO_2$.

22. The method of claim 20, wherein $R_1$ is a linear $C_2$–$C_{15}$ alkenyl group.

23. The method of claim 20, wherein $R_1$ is a $C_2$–$C_{15}$ epoxy group.

24. The method of claim 21, wherein $R_2$ is H.

25. The method of claim 21, wherein $R_2$ is $NO_2$.

26. The method of claim 22, wherein $R_2$ is H.

27. The method of claim 22, wherein $R_2$ is $NO_2$.

28. The method of claim 23, wherein $R_2$ is H.

29. The method of claim 23, wherein $R_2$ is $NO_2$.

30. The method of claim 21, wherein $R_1$ is a linear ethyl, propyl, butyl, hexyl or octyl group, and $R_2$ is H.

31. The method of claim 30, wherein $R_1$ is ethyl.

32. The method of claim 21, wherein $R_1$ is a linear methyl, ethyl or propyl group and $R_2$ is $NO_2$.

33. The method of claim 32, wherein $R_1$ is ethyl.

34. The method of claim 20, wherein $R_1$ is a $C_3$–$C_8$ cycloalkyl group.

35. The method of claim 34, wherein $R_2$ is H.

36. The method of claim 34, wherein $R_2$ is $NO_2$.

37. The method of claim 20, wherein $R_2$ is H, and $R_1$ is

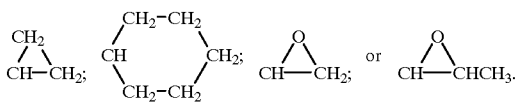

38. The method of claim 20, wherein $R_2$ is $NO_2$, and $R_1$ is

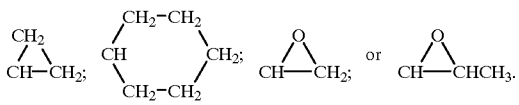

39. The method of claim 20, wherein transdermal administration is carried out by a patch containing a suspension or solution of said composition and said patch is brought into contact with said patient at a site away from the tumor location site.

* * * * *

UNITED STATES PATENT AND TRADEMARK OFFICE
CERTIFICATE OF CORRECTION

PATENT NO. : 6,120,793
DATED : September 19, 2000
INVENTOR(S) : Zhisong Cao and Beppino C. Giovanella It is certified that error appears in the above-identified patent and that said Letters Patent is hereby corrected as shown below:

<u>Title page, Item [54] and Column 1, lines 1 and 2,</u>
Delete the title, and insert -- DERIVATIVES OF CAMPTOTHECIN AND METHODS OF TREATING CANCER USING THESE DERIVATIVES. --

Signed and Sealed this

Twentieth Day of May, 2003

JAMES E. ROGAN
*Director of the United States Patent and Trademark Office*